US005843640A

United States Patent [19]
Patterson et al.

[11] Patent Number: 5,843,640
[45] Date of Patent: Dec. 1, 1998

[54] METHOD OF SIMULTANEOUSLY DETECTING AMPLIFIED NUCLEIC ACID SEQUENCES AND CELLULAR ANTIGENS IN CELLS

[75] Inventors: Bruce Patterson, Chicago; Steven Wolinsky, Glencoe; Michelle Till, Chicago, all of Ill.

[73] Assignee: Northwestern University, Evanston, Ill.

[21] Appl. No.: 521,467

[22] Filed: Aug. 30, 1995

Related U.S. Application Data

[63] Continuation-in-part of Ser. No. 245,530, May 18, 1994, which is a continuation of Ser. No. 901,702, Jun. 19, 1992, abandoned.

[51] Int. Cl.$^6$ ............................. C12Q 1/70; C12Q 1/68
[52] U.S. Cl. ............................. 435/5; 435/6; 435/7.1; 435/91.2
[58] Field of Search .................... 435/6, 91.2, 5, 435/7.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,770,992 | 9/1988 | Van de Engh et al. | 435/6 |
| 5,364,790 | 11/1994 | Atwood et al. | 435/288 |
| 5,436,144 | 7/1995 | Stewart et al. | 435/91.2 |
| 5,480,783 | 1/1996 | Haff | 435/91.2 |

FOREIGN PATENT DOCUMENTS

| | | |
|---|---|---|
| 0 237 362 | 9/1987 | European Pat. Off. . |
| 0 297 379 | 1/1989 | European Pat. Off. . |
| 0 310 229 | 4/1989 | European Pat. Off. . |
| 0 329 822 | 8/1989 | European Pat. Off. . |
| 0 369 775 | 5/1990 | European Pat. Off. . |
| 0 371 437 | 6/1990 | European Pat. Off. . |
| 0 373 960 | 6/1990 | European Pat. Off. . |
| 2711671 | 5/1995 | France ............... C12Q 1/68 |

OTHER PUBLICATIONS

Bagasra, O.; T. Seshamma; J. W. Oakes; and R. J. Pomerantz. 1993. *High Percentages of CD–4 Positive Lymphocytes Harbor The HIV–1 Provirus In The Blood Of Certain Infected Individuals.* Aids 7:1419–1423.

Banda, N. K.; J. Bernier; D. K. Kurahara; R. Kurrle; N. Haigwood; R. P. Sekaly; and T. H. Finkel. 1992. *Crosslinking CD4 By Human Immunodeficiency Virus gp120 Primes T Cells For Activation–Induced Apoptosis.* J. Exp.Med. 176:1099–1106.

Bank, I. and L. Chess. 1985. *Perturbation Of The T4 Molecule Transmits A Negative Signal To T–Cells.* J. Exp. Med., Oct. 1985. 162:1294–1303.

Butera, S. T.; V. L. Perez; B. Wu; G. J. Nabel; and T. M. Folks. 1991. *Oscillation Of The Human Immunodeficiency Virus Surface Receptor Is Regulated By the State Of Viral Activation In A CD4$^+$ Cell Model Of Chronic Infection.* J. Virol. 65:4645–4653.

Carmichael, A.; X. Jin; P. Sissons; and L. Borysiewicz. 1993. *Quantitative Analysis Of The Human Immunodeficiency Virus Type 1(HIV–1)–Specific Cytotoxic T Lymphocyte (CTL) Response At Different Stages Of HIV–1 Infection; Differential CTL Responses To HIV–1 And Epstein–Barr Virus In Late Disease.* J. Exp. Med. 177:249–256.

Clerici, M.; D. R. Lucey; J. A. Berzofsky; L. A. Pinto; T. A. Wynn; S. P. Blatt; M. J. Dolan; C. W. Hendrix; S. F. Wolf; and G. M. Shearer. 1993. *Restoration Of HIV–Specific Cell–Mediated Immune Responses By Interleukin–12 In Vitro.* Science 262:1721–1724.

Crise, B. and J. K. Rose. 1992. *Human Immunodeficiency Virus Type 1 Glycoprotein Precursor Retains A CD4–P56$^{ick}$ Complex In The Endoplasmic Reticulum* J. Virology. 2296–2301.

Doyle, C. and J. L. Strominger. 1987. *Interaction Between CD4 And Class II MHC Molecules Mediates Cell Adhesion.* Nature 330:256–259.

Embretson, J.; M. Zupancic; J. Beneke; M. Till; S. Wolinsky; J. L. Ribas; A. Burke; and A. T. Haase. 1993. *Analysis Of Human Immunodeficiency Virus–Infected Tissues By Amplification And In Situ Hybridization Reveals Latent And Permissive Infections At Single–Cell Resolution.* Proc. Natl. Acad. Sci. USA 90:357–361.

Embretson, J.; M. Zupancic; J. L. Ribas; A. Burke; P. Racz; K. Tenner–Racz; and A. T. Haase. 1993. *Massive Covert Infection Of Helper T Lymphocytes And Macrophages By HIV During The Incubation Period Of AIDS.* Nature (London) 362:359–362.

Fauci, A. S. 1988, *The Human Immunodeficiency Virus: Infectivity And Mechanisms Of Pathogenesis.* Science 239:617–622.

Fox, C. H.; K. Tenner–Racz; P. Racz; A. Firpo; P.A. Pizzo; and A.S. Fauci. 1991. *Lymphoid Germinal Centers Are Reservoirs Of Human Immunodeficiency Virus Type 1 RNA.* J. Infect. Dis. 164:1051–1057.

Garcia, J. V.; J. Alfano; and A. D. Miller. 1993. *The Negative Effect Of Human Immunodeficiency Virus Type 1 Nef On Cell Surface CD4 Expression Is Not Species Specific And Requires The Cytoplasmic Domain Of CD4.* J. Virol. 67(3): 1511–1516.

(List continued on next page.)

Primary Examiner—W. Gary Jones
Assistant Examiner—Amy Atzel
Attorney, Agent, or Firm—Dressler, Rockey, Milnamow & Katz, Ltd.

[57] ABSTRACT

In one aspect, the present invention provides an in situ process of simultaneously detecting a specific predetermined nucleic acid sequence and a specific predetermined cellular antigen in the same cell. In accordance with that process, the antigen is labeled with a biotin- or DNP-tagged antibody that specifically immunoreacts with the antigen, the specific nucleic acid sequences in the cell are amplified, the amplified nucleic acid sequences are labeled with a fluorescently-tagged nucleic acid probe that specifically hybridizes to the amplified nucleic acid sequences, and the labeled nucleic acid sequences and labeled cellular antigen are detected.

17 Claims, 12 Drawing Sheets

OTHER PUBLICATIONS

Gay, D.; P. Maddon; R. Sekaly; M. A. Talle; M. Godfrey; E. Long; G. Goldstein; L. Chess; R. Axel; J. Kappler; and P. Marrack. 1987. *Functional Interaction Between Human T Cell Protein CD4 And The Major Histocompatibility Complex HLA–DR Antigen.* Nature. 328: 626–629.

Glaichenhaus, N.; N. Shastri; D. R. Littman; and J. M. Turner. 1991. *Requirement For Association Of P56$^{lck}$ With CD4 In Antigen–Specific Signal Transduction In T Cells.* Cell 64:511–520.

Groux, H.; G. Torpier; D. Monté; Y. Mouton; A. Capron; and J. C. Ameisen. 1992. *Activation–Induced Death By Apoptosis In CD4$^+$ T Cells From Human Immunodeficiency Virus–Infected Asymptomatic Individuals.* J. Exp. Med. 175:331–340.

Gruters, R. A.; F. G. Terpstra; R. De Jong; C. J. M. Van Noesel; R. A. W. Van Lier; and F. Miedema. 1990. *Selective Loss Of T Cell Functions In Different Stages Of HIV Infection.* Eur. J. Immunol. 20:1039–1044.

Healey, D.; L. Dianda; J. P. Moore; J. S. McDougal; M. J. Moore; P. Estess; D. Buck; P. D. Kwong; P. C. L. Beverley; and Q. J. Sattentau. 1990. *Novel Anti–CD4 Monoclonal Antibodies Separate Human Immunodeficiency Virus Infection And Fusion Of CD4$^+$ Cells From Virus Binding.* J. Exp. Med. 172:1233–1242.

Hofmann, B.; K. Jakobsen; D. Odum; N.E. Dickmeiss; P. Platz; L.P. Ryder; C. Pedersen; L. Mathiesen; I. Bygberg; V. Faber; and A. Svejgaard. 1989. *Relatively Preserved Phytohemagglutinin As Opposed To Decreased Pokeweed Mitogen Responses Ay Be Due To Possibly Preserved Responses Via CD2/Phytohemagglutinin Pathway.* J. Immunol. 142:1874–1880.

Hoxie, J. A.; J. D. Alpers; J. L. Rackowski; K. Huebner; B. S. Haggarty; A. J. Cedarbaum; and J. C. Reed. 1986. *Alterations In T4 (CD4) Protein And mRNA Synthesis In Cells Infected with HIV.* Science 234:1123–1127.

Jabbar, M. A. and D. P. Nayak. 1990. *Intracellular Interaction Of Human Immunodeficiency Virus Type 1 (ARV–2) Envelope Glycoprotein Gp 160 With CD4 Blocks The Movement And Maturation Of CD4 To The Plasma Membrane.* J. Virology 64:6297–6304.

Koga, Y.; M. Sasaki; H. Yoshida; H. Wigzell; G. Kimura; and K. Nomoto. 1990. *Cytopathic Effect Determined By The Amount Of CD4 Molecules In Human Cell Lines Expressing Envelope Glycoprotein Of HIV.* J. Immunol144:94–102.

Koup, R. A.; J. R. Safrit; Y. Cao; C. A. Andrews; G. McLeod; W. Borkowsky; C. Farthing; and D. D. Ho. 1994. *Temporal Association Of Cellular Immune Responses With the Initial Control Of Viremia In Primary Human Immunodeficiency Virus Type 1 Syndrome.* J. Virol. 68:4650–4655.

Linette, G. P.; R. J. Hartzman; J. A. Ledbetter; and C. H. June. 1988. *HIV–1 Infected T Cells Show A Selective Signaling Defect Perturbation Of CD3/Anitgen Receptor.* Science. 241:573–576.

Maddon. P. J.; D. R. Littman; M. Godfrey; D. E. Maddon; L. Chess; and R. Axel. 1986. *The Isolation And Nucleotide Sequence Of A cDNA Encoding The T Cell Surface Protein T4: A New Member Of The Immunoglobulin Gene Family.* Cell 42:93–104.

Mariani, R. and J. Skowronski. 1993. *CD4 Down–Regulation By nef Alleles Isolated From Human Immunodeficiency Virus Type 1–Infected Individuals.* Proc. Natl. Acad. Sci. USA 90:5549–5553.

McDougal, J. S.; M S. Kennedy; J. M. Sligh; S. P. Cort; A. Mawle; and J. K. A. Nicholson. 1986. *Binding Of HTLV–III/LAV To CD4$^+$ Cells By A Complex Of The 110K Viral Protein And The T4 Molecule.* Science 231:382–385.

Pantaleo, G. C.; C. Graziosi; J. F. Demarest; L. Butini; M. Montroni; C. H. Fox; J. M. Orenstein; D. P. Kotler; and A. S. Fauci. 1993. *HIV Infection Is Active And Progressive In Lymphoid Tissue During The Clinically Latent Stage Of Disease.* Nature (London) 362:355–358.

Patterson, B. K.; C. Goolsby; V. Hodara; K. L. Lohman; and S. M. Wolinsky. 1995. *Detection Of CD4$^{30}$ T Cells Harboring Human Immunodeficiency Virus Type 1 DNA By Flow Cytometry Using Simultaneous Immunophenotyping and PCR–Driven In Situ Hybridization: Evidence Of Epitope Masking Of The CD4 Cell Surface Molecule In Vivo.* J. Virol. 69:4316–4322.

Patterson, B. K.; M. Till; P. Otto; C. Goolsby; M. R. Furtado; L. J. McBride; and S. M. Wolinsky. 1993. *Detection Of HIV–1 DNA And Messenger RNA In Individual Cells By PCR–Driven In Situ Hybridization And Flow Cytomery.* Science 260:976–79.

Piatak, M.; M. S. Saag; L. C. Yang; S. J. Clark; J. C. Kappes; K. C. Luk; B. H. Hahn; G. M. Shaw; and J. D. Lifson. 1993. *High Levels Of HIV–1 In Plasma During All Stages Of Infection Determined By Competitive PCR.* Science 259:1749–1754.

Poli, G.; P. Bressler; A. Kinter; E. Duh; W. C. Timmer; A. Rabson; J. S. Justement; S. Stanley; and A. S. Fauci. 1990. *Interleukin 6 Induces Human Immunodeficiency Virus Expression In Infected Monocytic Cells Alone And In Synergy With Tumor Necrosis Factor α By Transcriptional And Post–Transcriptional Mechansims.* J. Exp. Med. 172:151–158.

Rosenberg, Z. F. and A. S. Fauci. 1991. *The Immunopathogenesis Of HIV Infection.* The FASEB Journal 5:2382–2390.

Ryu, S. E.; P. D. Kwong; A. Truneh; T. G. Porter; J. Arthos; M. Rosenberg; X. Dai; N. Xuong; R. Axel; R. W. Sweet; and W. A. Hendrickson. 1990. *Crystal Structure Of An HIV–Binding Recombinant Fragment Of Human CD4.* Nature. 348:419–425.

Salmon, P.; R. Olivier; Y. Riviere; E. Brisson; J. C. Gluckman; M. P. Kieny; L. Montagnier; and D. Klatzmann. 1988. *Loss Of CD4 Membrane Expression And CD4 mRNA During Acute Human Immunodeficiency Virus Replication.* J. Exp. Med. 168:1953–1969.

Sattentau, Q.; A. G. Dalgleish; R. A. Weiss; P.C.L. Beverley. 1986. *Epitopes Of The CD4 Antigen And HIV Infection.* Science 234:1119–1123.

Seshamma, T.; O Bagasra; D. Trong; D. Baltimore; and R. J. Pomerantz. 1992. *Blocked Early–Stage Latency In The Peripheral Blood Cells Of Certain Individuals Infected With Human Immunodeficiency Virus Type 1.* Proc. Natl. Acad. Sci. USA 89:10663–10667.

Shaw; A. S.; K. E. Amrein; C. Hammond; D. F. Stern; B. M. Sefton; and J. K. Rose. 1989. *The Lck Tyrosine Protein Kinase Interacts With The Cytomplasmic Tail Of The CD4 Glycoprotein Through Its Unique Amino–Terminal Domain.* Cell 59:627–636.

Siliciano, R. F.; T. Lawton; C. Knall; R. W. Karr; P. Berman; T. Gregory; and E. L. Reinherz. 1988. *Analysis Of Host–Virus Interaction In AIDS With Anti–gp120 T Cell Clones: Effect Of HIV Sequence Variation And A Mechanism For CD4$^+$ Cell Depletion.* Cell 54;561–575.

Sodroski, J.;W. Chun Goh; C. Rosen; A. Dayton; E. Terwilliger; and W. Haseltine. 1986. *A Second Post–Transcriptional Trans–Activator Gene Required for HTLV–III Replication.* Nature 321:412–417.

Stevenson, M.; S. Haggerty; C. Lamonica; A. M. Mann; C. Meier; and A. Wasiak. 1990. *Cloning And Characterization Of Human Immunodeficiency Virus Type 1 Variants Diminshed In The Ability to Induce Syncytium–Independent Cytolysis.* J. Virol. 64:3792–3803.

Stevenson, M.; X. Zhang; and D. J. Volsky. 1987. *Downregulation Of Cell Surface Molecules During Noncytophathic Infection Of T Cells With Human Immunodeficiency Virus.* J. Virol. 61 (12):3741–3748.

Tyler, D. S.; S. D. Stanley; S. Zolla–Pazner; M. K. Gorny; P. P. Shadduck; A. J. Langlois; T. J. Matthews; D. P. Bolognesi; T. J. Palker; and K. J. Weinhold. 1990. *Identification Of Sites Within gp41 That Serve As Targets For Antibody–Dependent Cytotoxicity By Using Human Monoclonal Antibodies.* J. Immunol. 145:3276–3282.

Wei, X.; S. K. Ghosh; M. E. Taylor; V. A. Johnson; E. A. Emini; P. Deutsch; J. D. Lifson; S. Bonhoeffer; M. A. Nowak; B. H. Hahn; M. S. Saag; and G. M. Shaw. 1995. *Viral Dynamics In Human Immunodeficiency Virus Type 1 Infection.* Nature. 373:117–122.

Weiss, A. and D. R. Littman. 1994. *Signal Transduction By Lymphocyte Antigen Receptors.* Cell. 76:263–274.

Willard–Gallo K. E.; F. Van De Keere; and R. Kettmann. 1990. *A. Specific Defect In CD3γ–Chain Gene Transcription Results In Loss Of T Cell Receptor/CD3 Expression Late After Human Immunodeficiency Virus Infection Of A CD4$^+$ T Cell Line.* Proc. Natl. Acad. Sci. USA 87:6713–6717.

Yssel, H.; R. De Wall Malefyt; M. D. Dodon; D. Blanchard; L. Gazzolo; J. E. de Vries; and H. Spits. 1989. *Human T Cell Leukemia/Lymphoma Virus Type 1 Infection Of A CD4$^+$ Proliferative/Cytotoxic T Cell Clone Progresses In At Least Two Distinct Phases Based On Changes In Function And Phenotype Of The Infected Cells.* J. Immunol. 142:2279–2289.

Basgasra et al., Detection of Human Immunodeficiency Virus Type 1 Provirus in Mononuclear Cells by In Situ Polymerase Chain Reaction. *N. Eng. J. Med.* 326, 1385 (1992).

Bauman et al., Flow Cytometric Detection of Ribosomal RNA in Suspended Cells by Fluorescent In Situ Hybridization[1,2], *Cytometry* 9:515–524 (1988).

Dudin et al., A Method for Nuclei Acid Hybridization to Isolated Chromosomes in Suspension, *Hum. Genet* 76:190–292 (1987).

Folks et al., Biological and Biochemical Characterization of a Cloned LEU–3 Cell Surviving Infection with the Acquired Immune Deficiency Syndrome Retrovirus, *J. Exp. Med.* 164:280–290 (1986).

Harper et al., Detection of Lymphocytes Expressing Human T–lymphotropic virus Type III in Lymph Nodes and Peripheral Blood from Infected Individuals by in situ hybridization, *Proc. Natl. Acad. Sci. USA* 83;772–776 (1986).

Hsia et al., Human Immunodeficiency Virus DNA is Present in a High Percentage of CD4$^+$ Lymphocytes of Seropositive Individuals, *J. Infect. Dis.* 164:470–475.

Mullis et al., [21]Specific Synthesis of DNA in Vitro via a Polymerase–Catalyzed Chain Reaction, *Methods in Enzymo.* 155:335–350 (1987).

Ou et al. DNA Amplification for Direct Detection of HIV–1 in DNA of Peripheral Blood Mononuclear Cells, *Science* 238:295–297 (1988).

Pinkel et al., Cytogenetic Analysis by In Situ Hybridization with Fluorescently Labeled Nucleic Acid Probes. *Cold Spring Harbor Symposia on Quantative Bio.* LI:151–157 (1986).

Saiki et al., Enzymatic Amplification of β–Globin Genomic Sequences and Restriction Site Analysis for Diagnosis of Sickle Cell Anemia, *Science* 230:1350–1354 (1985).

Saiki et al., Primer–Directed Enzymatic Amplification of DNA with a Thermostable DNA Polymerase, *Science* 239:487–491 (1988).

Schnittman et al., The Reservoir for HIV–1 in Human Peripheral Blood Is a T Cell That Maintains Expression of CD4, *Science* 245:305–308 (1989).

Schnittman et al., Increasing Viral Burden in CD4$^+$ T Cells from Patients with Human Immunodeficiency Virus (HIV) Infection Reflects Rapidly Progressive Immunosuppression and Clinical Disease, *Ann. Intern. Med.* 113:438–443 (1990).

Gressens and Martin (Mar. 1994) *J. Neuropathol. Exp. Neurol.* 53:127–35.

Patterson et al. (1993) *Science* 260:976–79.

Van de Berg et al., (1991) *Laboratory Investigation* 64:623–628.

Nouvo and Forde (1995) *J. Histotechnology* 18:295–99.

Ou et al. (1988) *Science* 238:295–97.

Basgasra et al. (1992) *New England J. Medicine* 326:1385–91.

Harper et al. (1986) *Proc. Natl. Acad. Sci. USA* 83:772–76.

Bagasra et al. (1995) *Proc. Natl. Acad. Aci. USA* 92:12041–5.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 14
( D ) OTHER INFORMATION: /
/ label= K
/ note= "K = G or T/U"

( x i ) SEQUENCE DESCRIPTION: SEQ ID NO:1:

GCGAATTCAT GGAKCCAGTA GATCCTAGAC TA                32

( 2 ) INFORMATION FOR SEQ ID NO:2:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TTCTCTATCA AAGCAACCCA CCTCCCAATC                30

( 2 ) INFORMATION FOR SEQ ID NO:3:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

GCTCTAGACT ATCTGTCCCC TCAGCTACTG CTATGG            36

METHOD OF SIMULTANEOUSLY DETECTING AMPLIFIED NUCLEIC ACID SEQUENCES AND CELLULAR ANTIGENS IN CELLS

CROSS-REFERENCE TO APPLICATIONS

This application is a continuation-in-part application of U.S. patent application Ser. No. 08/245,530, filed on May 18, 1994, which is by itself a continuation of U.S. patent application Ser. No. 07/901,702, filed on Jun. 19, 1992 now abandoned. The disclosures of both these applications are incorporated herein by reference.

TECHNICAL FIELD OF THE INVENTION

The field of this invention is the detection of amplified nucleic acid sequences and cell antigens. More particularly, this invention relates to the simultaneous detection of these amplified nucleic acid sequences and antigens in cells, using microscopy or flow cytometry.

BACKGROUND OF THE INVENTION

Detection of viral nucleic acids in specimens comprising body fluids or tissues can be difficult because of the small quantity of viral DNA or RNA present in the specimen and/or because of the presence of other interfering materials, including DNA from a different source and ubiquitous RNases. These limitations may be overcome by employing the analytic method referred to as the polymerase chain reaction (PCR) technique. By this technique, selective enrichment of a specific DNA sequence can be achieved by exponential amplification of the target sequence. [See Mullis, et al., *Methods Enzymo.*, 155, 335 (1987); and Saiki, et al., *Science*, 230, 1350 (1985)].

To facilitate PCR amplification, pairs of oligonucleotide primers may be employed as described in U.S. Pat. Nos. 4,683,202 and 4,683,195. The primers are designed to hybridize with sequences that flank the target DNA. Following amplification, the amplified target sequence is detected by a hybridizing, target-specific probe. For example, this analytical procedure has been used for direct detection of HIV-1 (AIDS virus), as described by Ou, et al., *Science*, 238, 295–297 (January IS, 1988). The amplification cycles are facilitated by using a polymerase which is thermally stable in incubations up to 95 AGas described by Saiki, et al., *Science*, 239, 487–491 (Jan. 29, 1988).

Generally, specific amplified nucleic acids are detected by hybridization with labeled nucleic acid sequences complementary to a region within the amplified nucleic acid. Thus, the whole population of amplified nucleic acids are simultaneously detected. When in situ procedures (e.g., PCR) are used to detect nucleic acid sequences in cells, the severity of the procedures per se obviate the simultaneous detection of other cellular components such as cellular antigens. For example, the extended thermal cycling needed for amplification of nucleic acids by PCR destroys or alters heat labile structures such as protein receptors and enzymes.

Other measurement techniques, however, allow the analysis of individual cells. These techniques included microscopy and flow cytometry. Flow cytometry involves analyzing cells or cellular fractions (stained with fluorescent dyes) suspended in a solution. In flow cytometry, cells are forced in a narrow stream through a path of laser light. The cells pass the laser beam in single file at a rate up to several thousands per second. When cells enter the light, they scatter light or emit fluorescence. As each cell passes through the light source, its optical properties are quantified and stored with this technique. A large number of cells can be measured characterized individually in a short period of time.

Van den Engh et al., U.S. Pat. No. 4,770,992 show detection of DNA sequences in chromatin by flow cytometry. The method disclosed by Van den Engh et al., however, does not allow for the detection of short target sequences or nucleic acids located in the cytoplasm. To make these assessments an intact cell must be analyzed.

Quantification of viral burden in patients with a infection is relevant for prognostic and therapeutic purposes. For example, several studies have attempted to quantify Human Immunodeficiency Virus (HIV-1) DNA or PNA using co-amplification of HIV-1 GAG and HLA-DQ- '[See T. Lee, F. J. Sunzeri, L. H. Tobler, et al., *Aids* 5, 683 (1991)], quantitative PNA PCR [See L. Q. Zhang, P. Simmonds, C. A. Ludlam, A. J. L. Brown, *Aids* 5, 675 (1991)], and quantitative DNA PCR following cell sorting [See S. M. Schnittman, M. C. Psallidopoulos, H. C. Lane, et al., *Science* 245, 305 (1989)]. In addition, histologic methods such as in situ hybridization using cPNA probes complementary to, HIV-1 PNA [See M. E. Harper, L. M. Marselle, R. C. Gallo, F. Wong-Staal, *Proc Natl Acad Sci USA* 83, 772 (1986)] and in situ PCR for HIV-1 proviral DNA [See O. Basgasra, S. P. Hauptman, H. W. Lischner, M. Sachs, R. J. Pomerantz, *N Engl J Med* 326, 1385 (1992)] have been used to directly identify infected peripheral mononuclear cells isolated from patients. Due to the markedly discordant results in these studies only limited insight is gained into the percent of infected cells in HIV-1 patients with estimates ranging anywhere from 10% of cells in symptomatic patients containing HIV-1 DNA [See K. Hsia, S. A. Spector, *J Infect Dis* 164, 470 (1991)] to between 1 in 100 and 1 in 100,000 cells in asymptomatic carriers containing HIV-1 [See S. N. Schnittman, J. J. Greenhouse, N. C. Psallidopoulos, *Ann Intern Med* 113, 438 (1990)]. Additionally, the lack of consistent data confuses interpretations of the role that this determination plays in disease progression and prognosis.

Previous attempts to combine nucleic acid hybridization with flow cytometry have been restricted by target copy number or sequence specificity. Solution hybridization and flow cytometric detection of positively hybridized nuclei has been reported utilizing either total genomic DNA [See G. Dudin, T. Cremer, M. Schardin et al., *Hum Genet* 76, 290 (1987)] or highly repetitive chromosome specific sequences [See D. Pinkel, J. W. Gray, B. Trask, *Cold Spring Harbor Symposia on Quantitative Biology*, Vol. LI., 151 (1986)] as probes. Additionally, flow cytometric detection of hybridization to ribosomal PNA has been successful [See J. G. Bauman et al., *Cytometry* 9:515–524 (1988)] and detection of a high abundance mRNA; -actin in L929 cells has been reported [See E. A. Timm, Jr., C. C. Stewart, *Biofeedback* 12, 363 (1992)].

The present invention provides a process that combines the sensitivity of in situ polymerase chain reaction, the specificity of nucleic acid hybridization, and the specificity and stability of biotin- or DNP-tagged antibodies against cellular antigens with the rapid and quantitative single cell analytic capability of flow cytometry. Unlike in situ polymerase chain reaction technique performed on cells adhered to slides, the solution based process described herein allows for the multi-parameter analysis of large numbers of cells by flow cytometry and further characterization following cell sorting. Using this technique, we have detected a single HIV-1 proviral sequence per cell in an HIV-1 positive cell line and HIV-1 proviral, HIV test mRNA sequences simultaneously with CD4 and CD83 in HIV-1 infected patients.

BRIEF SUMMARY OF THE INVENTION

In one aspect, the present invention provides an in situ process of simultaneously detecting a specific predetermined nucleic acid sequence and a specific predetermined cellular antigen in the same cell. That process comprises the steps of (a) labeling the antigen with a biotin- or DNP-tagged antibody that specifically immunoreacts with the antigen, (b) amplifying the specific nucleic acid sequences in the cell, (c) labeling the amplified nucleic acid sequences with a fluorescently-tagged nucleic acid probe that specifically hybridizes to the amplified nucleic acid sequences, and (d) detecting the labeled nucleic acid sequences and labeled cellular antigen.

The specific nucleic acid sequence can be a DNA sequence or a RNA sequence. A preferred nucleic acid sequence is a viral nucleic acid sequence. The viral nucleic acid sequence is preferably an HIV sequence such as HIV-1 proviral DNA or mRNA.

A preferred cellular antigen is a cell surface antigen. In one embodiment, the cell surface antigen is a cell surface antigen involved in T cell activation such as CD4.

A process of this invention is particularly useful in detecting nucleic acid sequences and cellular antigens in white blood cells. In one embodiment, the white blood cells are peripheral mononuclear cells such as T cells.

In a preferred embodiment, amplification of nucleic acid sequences is accomplished in solution using deoxyribonucleotide triphosphates coupled to a bulky molecule that prevents diffusion of amplified sequences from the cell. Detecting the labeled nucleic acid sequences and cellular antigen is accomplished by fluorescence activated flow cytometry or fluorescence microscopy.

In a preferred embodiment therefore, the present invention provides an in situ process of simultaneously detecting a specific predetermined nucleic acid sequence and a specific predetermined cellular antigen in the same cell, the process comprising the steps of (a) labeling the antigen with a biotin- or DNP (dinitrophenol)-tagged antibody that specifically immunoreacts with the antigen, (b) exposing the antigen-labeled cell to a fixative and permeabilization agent, (c) amplifying the specific nucleic acid sequences in the cell in the presence of deoxyribonucleotide triphosphates coupled to a molecule that prevents diffusion of amplified sequences from the cell, (d) labeling the amplified nucleic acid sequences with a fluorescently-tagged nucleic acid probe that specifically hybridizes to the amplified nucleic acid sequences, and (e) detecting the labeled nucleic acid sequences and labeled cellular antigen.

In another aspect, the present invention provides an in situ process of simultaneously detecting HIV-1 proviral DNA and cell surface CD4 antigen in T cells, the process comprising the steps of (a) labeling the CD4 cell surface antigen of the T cells with a biotin- or DNP-tagged antibody that specifically immunoreacts with the CD4 cell surface antigen, (b) exposing the antigen-labeled cells to a fixative and permeabilization agent, (c) amplifying the HIV-1 proviral DNA nucleic acid sequences in the cells in the presence of deoxyribonucleotide triphosphates coupled to a molecule that prevents diffusion of amplified sequences from the cell, (d) labeling the amplified HIV-1 proviral DNA sequences with a fluorescently-tagged nucleic acid probe that is complementary to the HIV-1 proviral DNA sequences, and (e) detecting the labeled HIV-1 proviral DNA nucleic acid sequence and labeled CD4 cell surface antigen by fluorescence activated flow cytometry.

BRIEF DESCRIPTION OF THE DRAWINGS

The file of this patent contains at least one drawing executed in color. Copies of this patent with color drawings(s) will be provided by the Patent and Trademark Office upon request and payment of necessary fee.

DETAILED DESCRIPTION OF THE INVENTION

Figure 1:
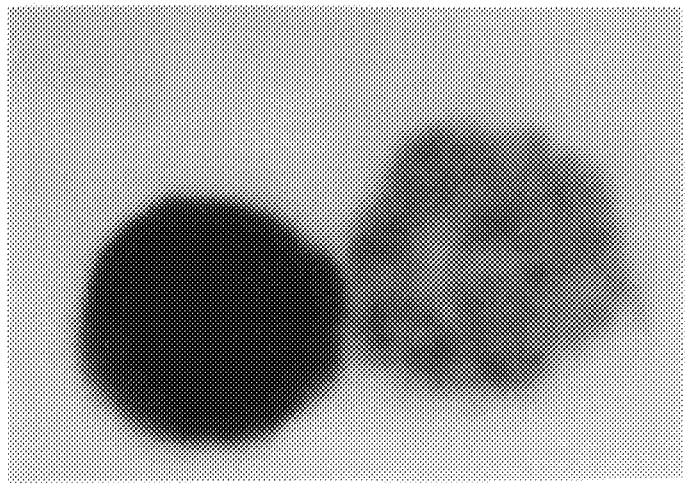
FIG. 1. Shows in situ PCR using primers SK38/39 on 8E5/LAV cells diluted to 50% using seronegative peripheral mononuclear cells. Amplificate remains in positive cells (dark brown) and negative cells contain no amplified product (light green). Color development was achieved using an alkaline phosphatase conjugated anti-digoxigenin antibody which binds to digoxigenin incorporated in the amplificate. The substrate NBT/xphosphate precipitates to form a brown product. Cells were counter-stained with Fast Green.

In one aspect, the present invention provides an in situ process of simultaneously detecting a specific predetermined nucleic acid sequence and a specific predetermined cellular antigen in the same cell. That process comprises the steps of (a) labeling the antigen with a biotin- or DNP-tagged antibody that specifically immunoreacts with the antigen, (b) amplifying the specific nucleic acid sequences in the cell, (c) labeling the amplified nucleic acid sequences with a fluorescently-tagged nucleic acid probe that specifically hybridizes to the amplified nucleic acid sequences, and (d) detecting the labeled nucleic acid sequences and labeled cellular antigen.

The specific nucleic acid sequence can be a DNA sequence or a RNA sequence. A process of the present invention has been shown to be particularly useful in detecting viral nucleic acid sequences. As set forth hereinafter in the Examples, a process of the present invention has been used to detect an HIV nucleic acid sequence, HIV-1 proviral DNA, in white blood cells. One of ordinary skill in the art will readily appreciate, however, that a process of the present invention can be used to detect other nucleic acid sequences in other cells and tissues (e.g. translocations in leukemic of fetal cells in maternal circulation).

The presence of any cellular antigen can be detected using a process of this invention. The present invention has particular utility for detecting antigens that are expressed on the surface of cells (i.e., a cell surface antigen).

In a similar manner, while the present invention can be used to detect nucleic acid sequences and cellular antigens in any cell type, that process is particularly useful where the cells are white blood cells. In one embodiment, the white blood cells are peripheral mononuclear cells. An especially preferred peripheral mononuclear cell is a T cell. Where the cell is a T-cell, a preferred cell surface antigen detectable by a process of this invention is a cell surface antigen involved in T cell activation such as CD4. It is preferable to use a process of the present invention on cells that have been separated from other cell types. Means for preparing isolated groups of particular cells are well known in the art.

The cellular antigen is labeled with a biotin- or DNP-tagged antibody that specifically immunoreacts with the antigen to be detected. Monoclonal antibodies are preferred because of their high degree of immunospecificity. Means for tagging or labeling molecules such as antibodies with biotin are well known in the art. The present invention discloses that the labeling of cellular antigens with a biotin- or DNP-tagged antibody allows the label to survive the subsequent steps used to amplify and label nucleic sequences. The use of a biotin- or DNP-tagged antibody to label CD4 on T cells is described in detail hereinafter in Example 3.

A preferred means for amplifying a specific nucleic acid sequence is the polymerase chain reaction (PCR) technique (U.S. Pat. Nos. 4,683,202 and 4,683,195 hereby incorporated by reference). Other amplification techniques may also be used to practice this invention. See e.g. Erlich et al. EP 0 237 362, Dattagupta et al. EP 0 297 379, Becker EP 0 300 769, Burg et al. 0 310 229, Collins EP 0 328 822, Davey 0 329 822, Loewy et al. EP 0 369 775, EP 0 371 437, Gingeras EP 0 373 960, and Rose et al. EP 0 379 639.

The polymerase chain reaction amplification procedure is conducted as disclosed in U.S. Pat. Nos. 4,683,202 and 4,683,195. To facilitate retaining amplified product within the cell after application of proteinase K and thermal cycling, deoxyribonucleotide triphosphates are coupled to bulky molecules such as digoxigenin. We have found that the incorporation of these molecules during amplification provides a way to detect amplified DNA in a cell in solution because these molecules function to prevent amplified product from leaking out of the cell.

Amplification localization and optimization of cycling parameters were evaluated using an antibody to the compound coupled to the deoxyribonucleotide triphosphates. In particular, for detection of HIV-1-DNA certain primers SK38/39 (GAG) and SK68/69 (ENV) provides the greatest sensitivity and specificity. Additionally, the concentration of magnesium also affected sensitivity and specificity.

This technique can be used to detect specific nucleic acid sequences such as HIV-1 proviral DNA, HIV-1 RNA, HLA-DQ, and potentially T-cell receptor and B-cell gene rearrangements.

In a preferred embodiment, amplification of nucleic acid sequences is accomplished in solution using deoxyribonucleotide triphosphates coupled to a bulky molecule that prevents diffusion of amplified sequences from the cell. Detecting the labeled nucleic acid sequences and cellular antigen is accomplished by fluorescence activated flow cytometry or fluorescence microscopy.

Where a cellular antigen is simultaneously detected with an amplified nucleic acid sequence, the thermal cycling parameters are modified so as to minimize autofluorescence and autofluorescence convection. It is preferred that less than about 30 thermal cycles are used. Where a biotin- or DNP-tagged antibody against CD4 was used to detect CD4 on T-cells, 25 thermal cycles were used (See Example 3 hereinafter). One of ordinary skill in the art can readily determine the appropriate number of thermal cycles for a given nucleic acid and cellular antigen.

In accordance with a preferred embodiment of the present invention, amplified nucleic acid sequences and antigens in cells are simultaneously detected using flow cytometry. When working with a flow cytometer, generally a specific class of cells are transported through the instrument. This invention specifically relates to the detection of certain preselected nucleic acid sequences and cellular antigens in peripheral blood mononuclear cells, but other classes of cells such as monocytes, thymocytes and digested tissues can also be used.

The isolated cells are adjusted to a suitable concentration for detection such as $1 \times 10^6$ cells/ml. The cells are typically treated with a water soluble fixative such as STF (Streck Laboratories) or Permafix (Ortho diagnostics). STF is a proprietary fixative agent containing acetic acid and zinc. A dilution suitable for peripheral blood mononuclear cells was about the same as recommended for general tissue staining, i.e., about 1.0x. Means for determining suitable concentrations for other cells are well known in the art. To assess concentration of the fixative agent both the morphology of the cell and the efficacy of amplification are considered as is also well known in the art.

The following examples illustrate preferred embodiments of the present invention and are not limiting of the claims or specification.

EXAMPLE 1

Detection of HIV-1 Proviral DNA

Cell Lines and Viruses: 8E5/LAV cells are an established cell line containing a single copy of HIV-1 proviral DNA. 8E5/LAV is available from ERC Bioservices Corporation—catalog number 95. This reagent was obtained through the AIDS Research End Reference Reagent Program, Division of AIDS, NIAID, NIHS 8E5/LAV from Dr. Thomas Folks. Folks, T. M. Powell, D., Lightfoote, M. Koenig, S., Fauci, A. S., Benn, S., Rabson A., Daugherty, D., Gendelman, H. E., Hoggan, M. D., Venkatesan, S., and Martin, M. A., Biological and biochemical characterization of a cloned Leu-3-cell surviving infection with the acquired immune deficiency syndrome retrovirus. *J. Exp. Med.* 164: 280–290, 1986. The growth characteristics are provided in a data sheet that accompanies a shipment of the cell line.

8E5/LAV, an established cell line having one HIV-1 proviral DNA molecule per cell, was used to prepare a copy number standard curve for polymerase chain reaction amplification. Low passaged 8E5/LAV cells are maintained in suspension culture in RPMI 1640 media (Gibco Laboratories) supplemented with 20% fetal bovine serum (Hyclone Labs), 2 mM L-glutamine, and penicillin (100 units/ml) streptomycin (100 micrograms) in a humidified incubation with a 5% $CO_2$ atmosphere.

HIV-1 negative peripheral mononuclear cells were separated from the whole blood of normal healthy donors who were in a low risk for AIDS and who had been screened as negative for HIV-1 antigen/antibody and for Hepatitis B surface antigen. Mononuclear cells were separated from heparinized whole blood by centrifugation on a LYMPHOCYTE SEPARATOR medium (Organon Teknike Corporation) gradient.

The layer containing the peripheral mononuclear cells was removed and washed three times with Dulbecco's phosphate buffered saline, magnesium and calcium free (D-PBS, Gibco Laboratories) Cell suspensions of the positive control cells, 8E5/LAV, negative cells, and HIV-1 positive clinical samples was quantified by hemocytometer counting until duplicate counts were within 5% of each other. The concentration of cell suspensions was adjusted to $1 \times 10^6$ cells per milliliter with D-PBS. Four hundred microliters of this suspension is equivalent to 400,000 cells and in the case of 8E5/LAV cells is equivalent to 400,000 copy numbers of HIV-1 proviral DNA. Standard of curve dilution medium consisted of the HIV-1 negative peripheral blood mononuclear cells ($1 \times 10^6$ cells/milliliter) D-PBS.

Several dilutions of 8E5/LAV cells were made in the standard curve dilution medium of negative peripheral mononuclear cells to obtain standard curve point of 50,000, 100,000, 200,000, and 400,000 copy numbers. The zero copy number point was HIV-1 negative peripheral mononuclear cells alone. Using a dilution medium of negative peripheral blood mononuclear cells ensured a consistent total number of cells in each polymerase chain reaction amplification tube. Four hundred microliters of each standard curve dilution and clinical sample was aliquoted in 0.5 ml microfuge tube (Eppendorf) for in situ polymerase chain reaction.

Peripheral blood mononuclear cells were isolated from fresh heparinized blood layered on a HISTOPAQUE 077 (Sigma, St. Louis, Mo.) density gradient. This gradient was centrifuged for 30 min. in GH-37 rotor at 1600 rpm at room temperature. The turbid mononuclear layer was removed and transferred to clean 15 ml. conical tube. The cells were washed twice with three volumes of RPMI and once with phosphate buffered saline (pH 7.6).

In situ Polymerase Chain Reaction: cell samples were adjusted to a concentration of $1 \times 10^6$ cells/ml and 400 $\mu$l of each sample was pelleted at 1500 rpm for two min. After removal of the supernatant, the cells were re-suspended in 50 $\mu$l of STF (Streck Laboratories, Omaha, Nebr.) fixative and incubated at room temperature for fifteen min. Cells were again pelleted at 1500 rpm for two min. re-suspended in 25 $\mu$l of 1 $\mu$g/ml proteinase K in 0.1M Tris HCL, 50 mM EDTA (pH 8.0), and incubated at 37° C. for fifteen min. Cells were pelleted as above, washed twice with phosphate buffered saline (pH 7.4) and placed on ice. 190 $\mu$l of polymerase chain reaction mixture (10 mM Tris HCL pH 8.3, 50 mM KCL, 1.5 mM MgCl, 0.25 mM dATP, dCTP, dGTP, 0.14 mM dTTP, 4.3 $\mu$M dUTP-11-digoxigenin (Genius 1 DNA labeling and Detection Kit (hereby incorporated by reference), 100 pmole each forward and reverse primer (SK 38/39 Primers) 1.0 $\mu$l (5$\mu$) Taq polymerase (Amplitaq, Perkin Elmer, Norwalk, Conn.) and gelatin 0.001% w/v was added to said sample.

Samples were placed in a Perkin Elmer Cetus automated thermocycler once block temperature reached 80° C., then cycled. Thermal cycling parameters (optimal) were as follows: denaturation-94° C., one min., reannealing 58° C., two min., extension-74AC.1.5 min. with five sec. added for each successive extension cycle. Cells were cycled for 40 cycles and stored at 4° C. after cycling if necessary. Amplification localization and optimization of cycling parameters were evaluated using an antidigoxigenin alkaline phosphatase conjugated antibody. See FIG. 1 and Table 1. Briefly, amplified cells were cytospun onto poly-L-lysine coated slides, washed with phosphate buffered saline pH 7.4 and incubated with the conjugated antibody for two hours at 37° C. Cells were washed as above and incubated with substrate (NBT/X-phosphate) for 10 min. at room temperature. Cells were counter-stained with FAST GREEN (Rowley Biochemical Institute, Rowley, Mass.) and cover-slipped.

TABLE I

OPTIMIZATION OF *IN SITU* PCR CYCLING CONDITIONS USING IMMUNOHISTOCHEMICAL DEVELOPMENT

| PRIMERS | [Mg] | Sensitivity | Specificity |
| --- | --- | --- | --- |
| GAG | 1.5 mM | 100% | 98% |
| (SK38/39) | 2.25 mM | 100% | 95% |
| ENV | 1.5 mM | 98% | 94% |
| (SK68/69) | 2.25 mM | 100% | 91% |

Solution hybridization. Sequence specific oligonucleotide probes (Applied Biosystems, San Diego, Calif.) SK19-FITC) containing multiple fluorescence tagged nucleotides were added to the polymerase chain reaction tubes (400 pmol/tube) along with 10 $\mu$g/ml sonicated herring sperm DNA. Tubes were heated to 94° C. for two min. and hybridization was performed for two hrs. at 56° C. Cells were washed under high stringency for thirty min. with 2×SSC/50% formamide/500 $\mu$g/ml bovine serum albumin at 42° C., 30 minutes with 1×SSC/50% formamide/500 $\mu$g/ml bovine serum albumin at 42° C., thirty min. with 1×SSC/500 $\mu$g/ml bovine serum albumin at room temperature, and briefly with phosphate buffered saline temperature. Cells were re-suspended in phosphate buffered saline pH 8.3 and counter-stained for flow cytometric analysis with 1 $\mu$g/ml propidium iodide.

Flow Cytometric Analysis

Figure 2:
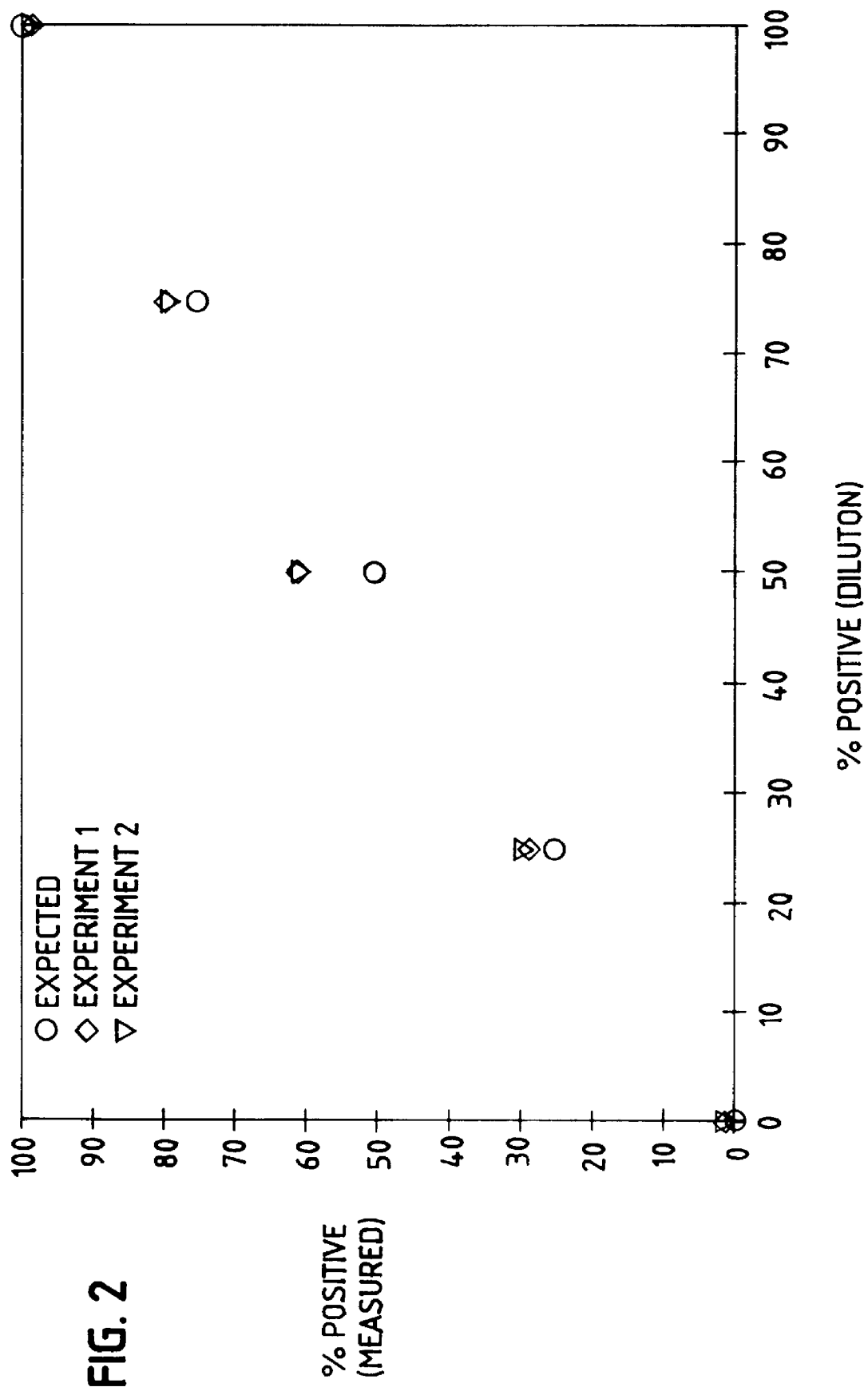
FIG. 2. Standard curve of 8E5/LAV cells (HIV-1 positive) diluted with seronegative peripheral mono-nucleic cells as determined by in situ PCR and flow cytometric analysis (y-axis).
Figure 3:
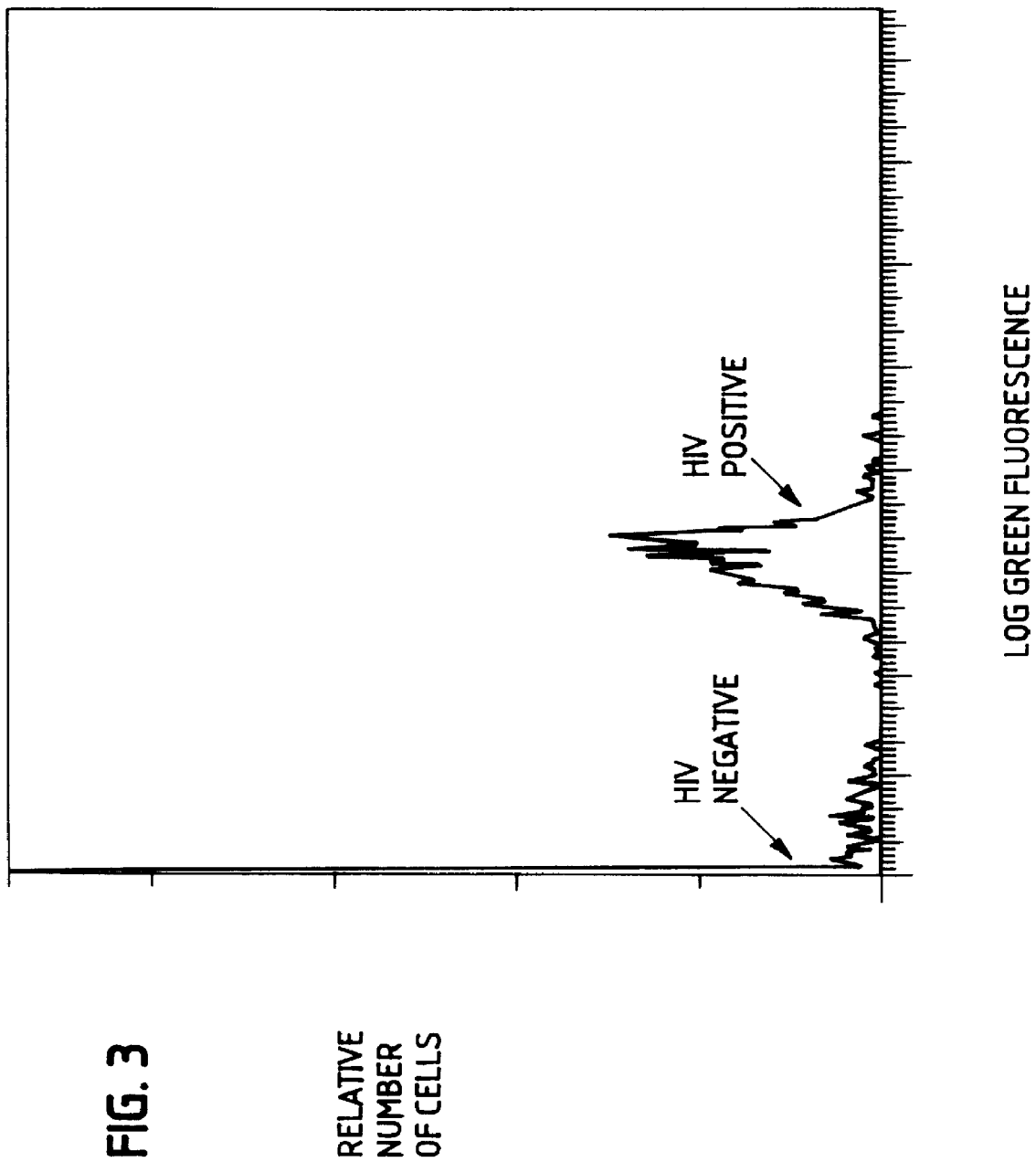
FIG. 3. Fluorescence histogram showing HIV-1 positive and HIV-1 negative cells quantitated by in situ PCR and flow cytometric analysis.
Figure 4A:
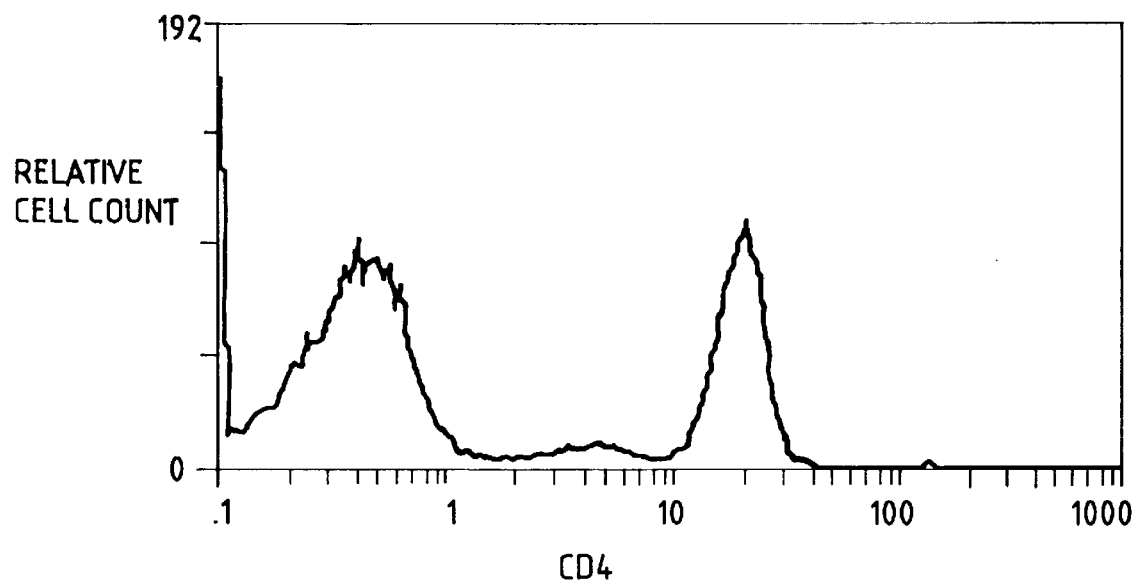
FIG. 4 shows the effectiveness of various antibody conjugation and binding schemes on cells subjected to thermal amplification in situ. The histogram in row B was generated using cells with antibody bound following fixation and permeabilization but before thermal amplification. The histogram in row C was generated using cells with antibody bound before fixation and permeabilization followed by thermal amplification. In row C, column A, strepavidin-phycoerythrin was added after thermal amplification and hybridization. The histogram in row D was generated using cells with antibody bound following fixation, permeabilization, and thermal amplification.
Figure 4B:
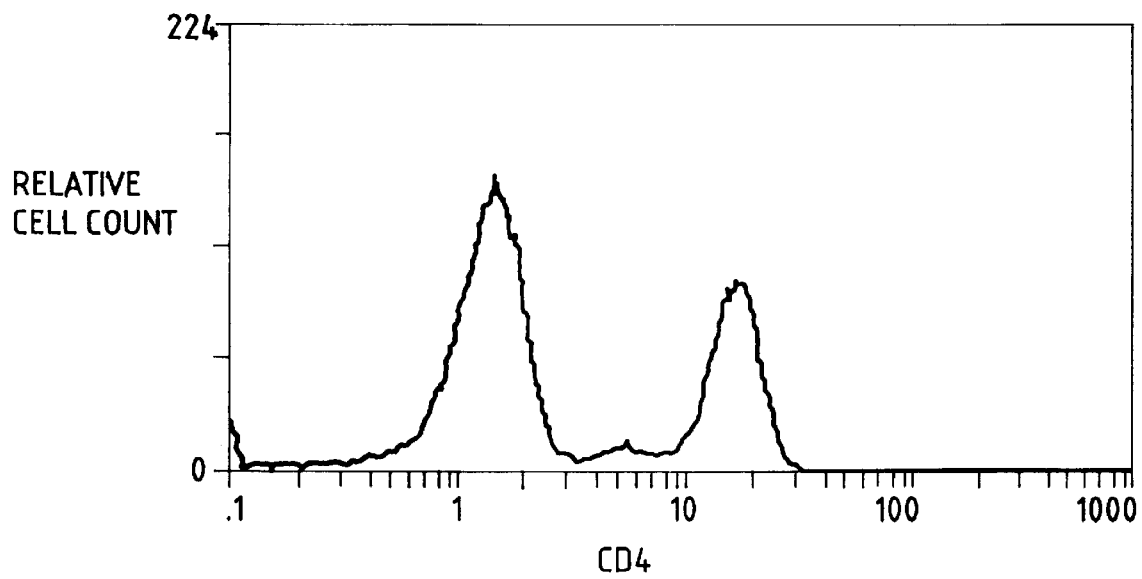
Figure 4C:
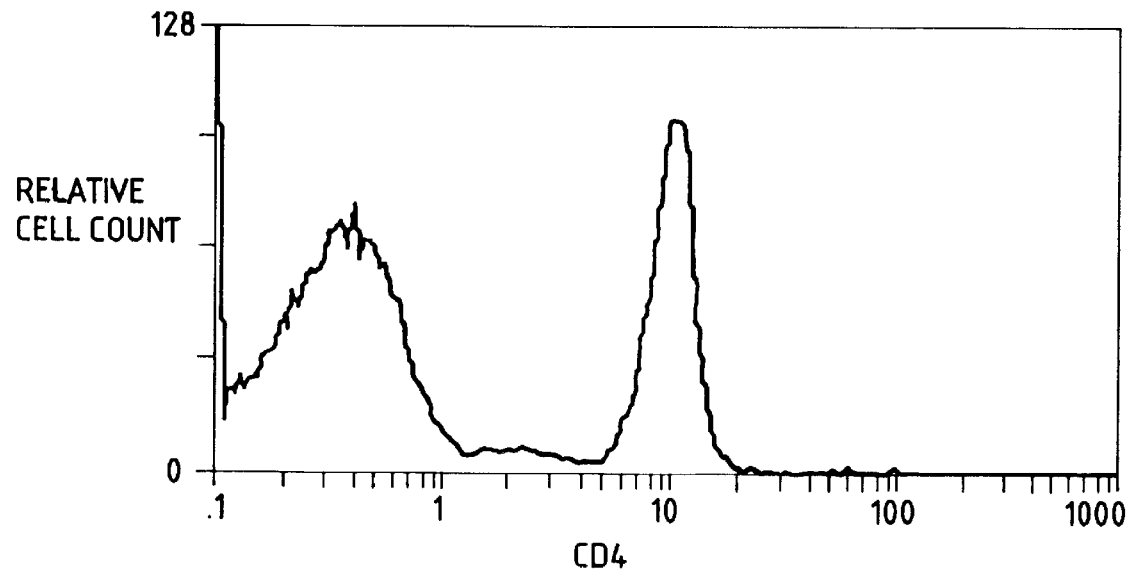
Figure 4D:
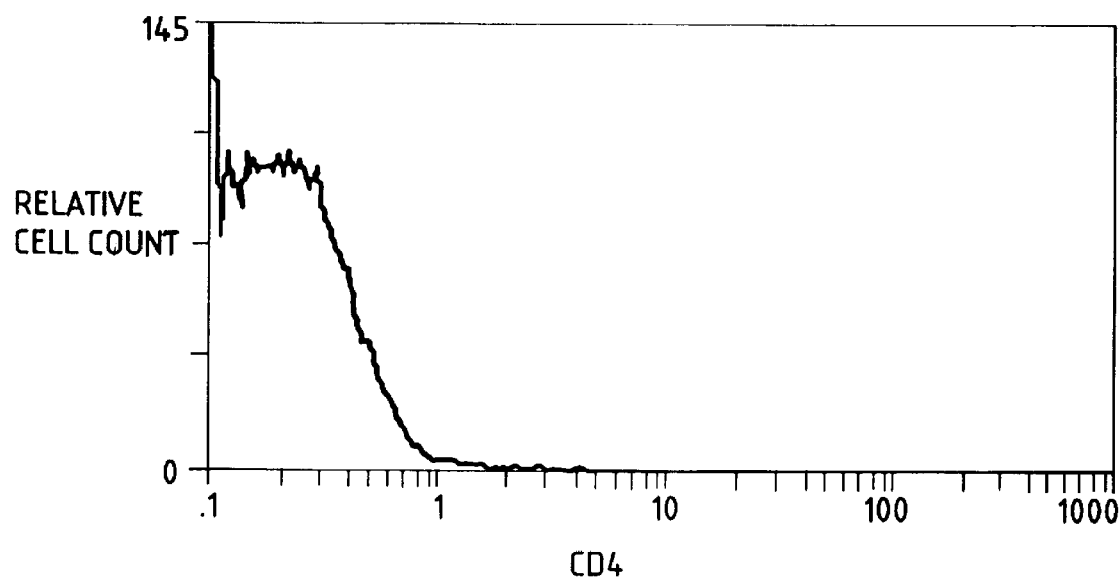
Figure 5A:
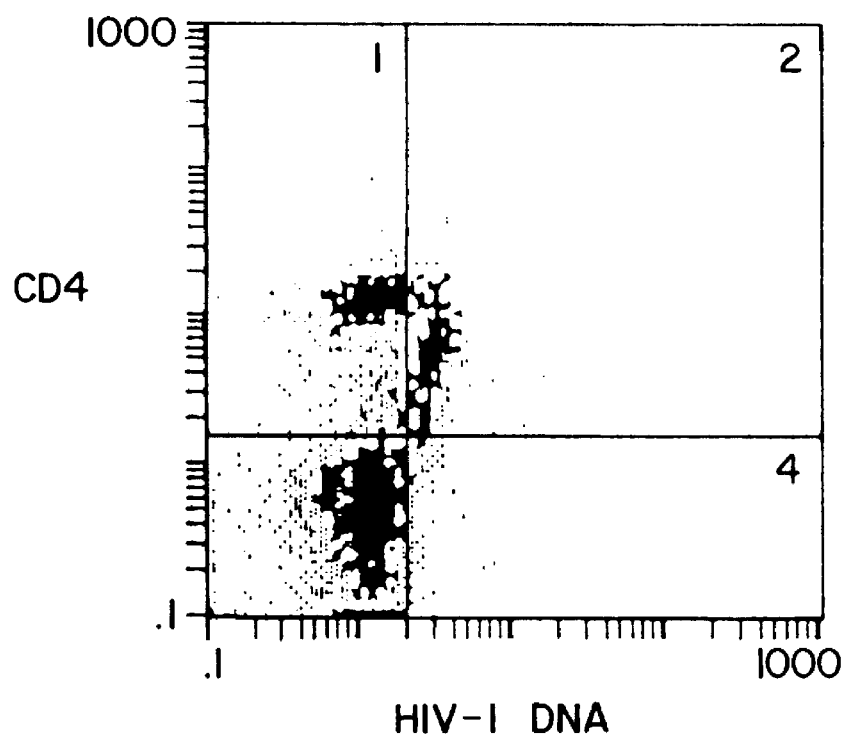
FIG. 5 shows a comparison of representative dual color dot plots of monocyte-depleted PBMCs from patients with varying CD4 counts. Simultaneous immunophenotyping and PCR-driven in situ hybridization was performed on monocyte-depleted PBMCs as described using the anti-CD4 antibody, Leu3A. The double positive (CD4 positive, HIV-1 DNA positive) populations for each sample are in quadrant 2 of each plot. The patient sample numbers and CD4 counts which correspond to Table 1 are: (A) patient #13, CD4 T-cell count of 1431, (B) patient #12, CDr+T-cell count of 742, (C) patient #6, CD4+T-cell count of 263, and (D) patient #9, CD4+T-cell count of 506.
Figure 5B:
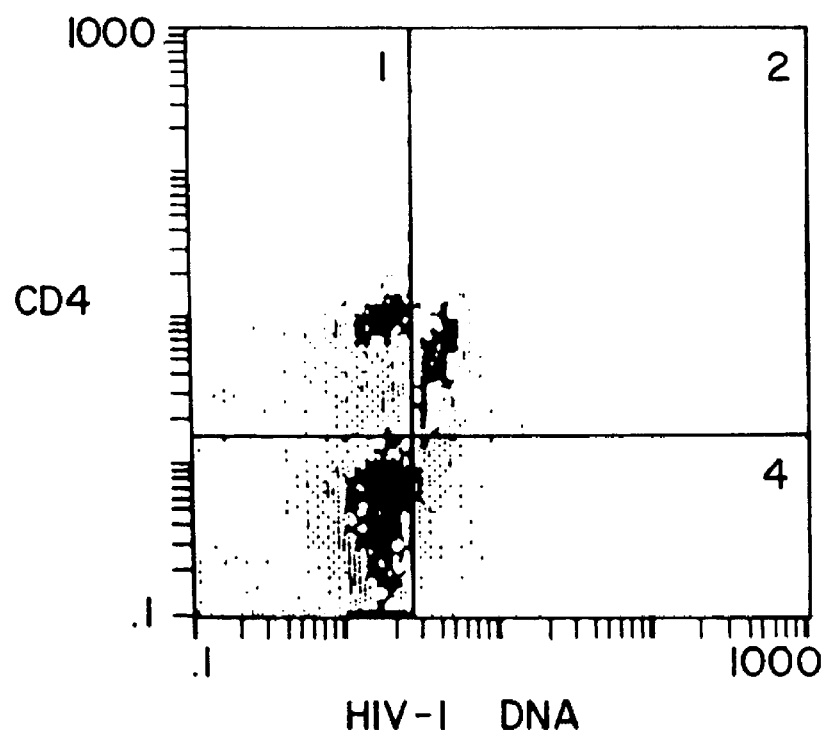
Figure 5C:
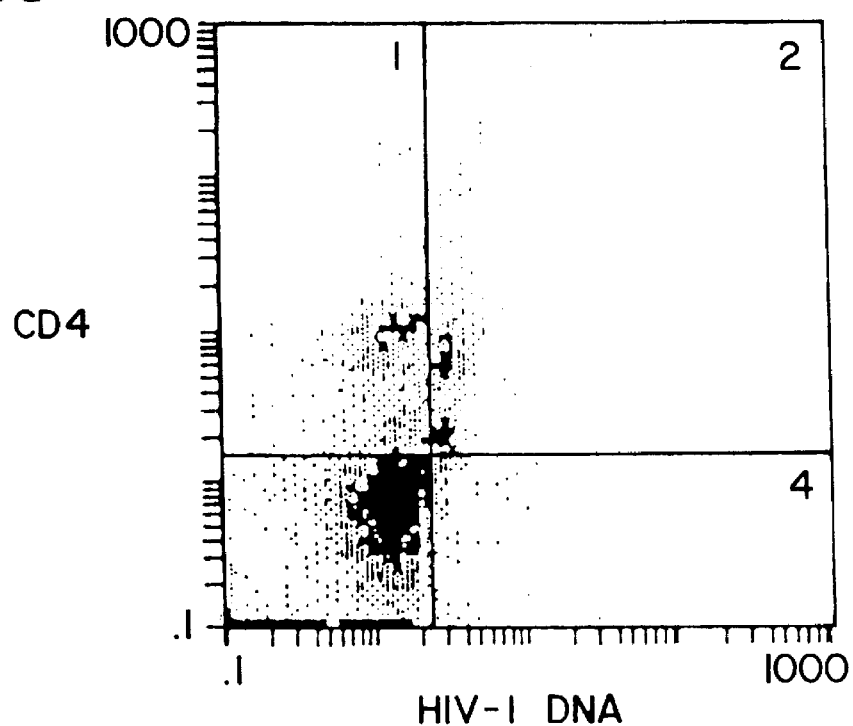
Figure 5D:
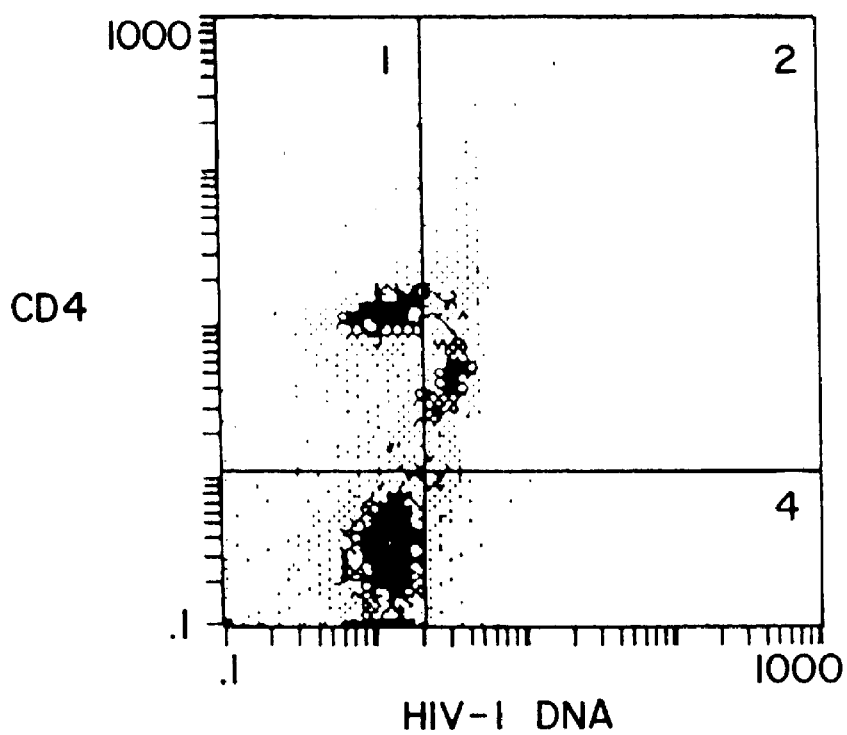
Figure 6A:
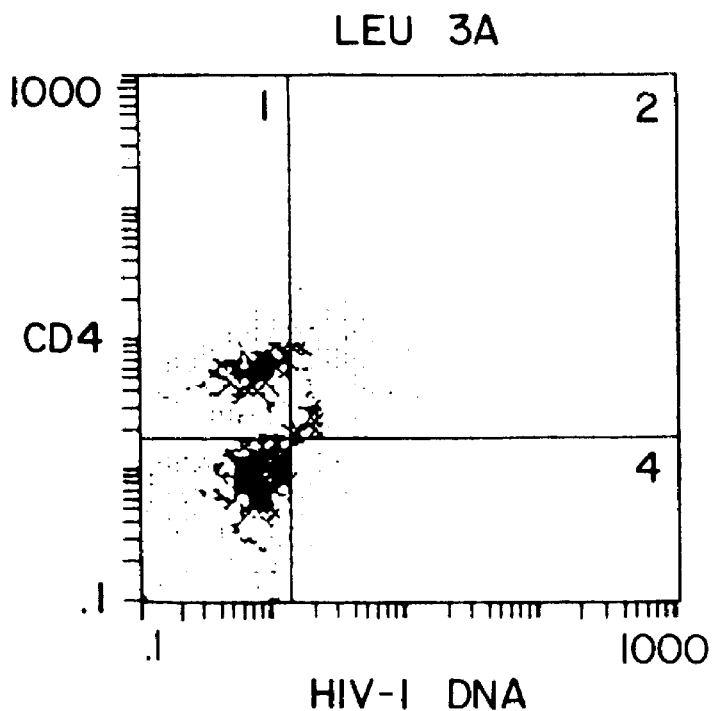
FIG. 6 shows plots from patient 13 (A) and patient 4 (B) showing a decrease in Leu3A staining without a decrease in L120 staining in the CD4 negative, HIV-1 DNA positive cell population. The dot plots from an HIV-1 seronegative control patient 14(C) revealed no difference in Leu 3A staining intensity when compared to L120 staining.
Figure 6B:
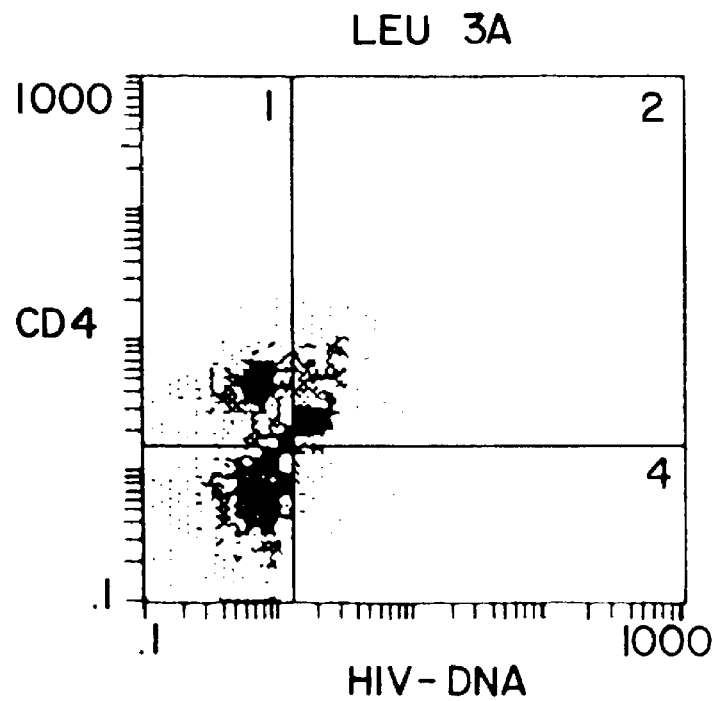
Figure 6C:
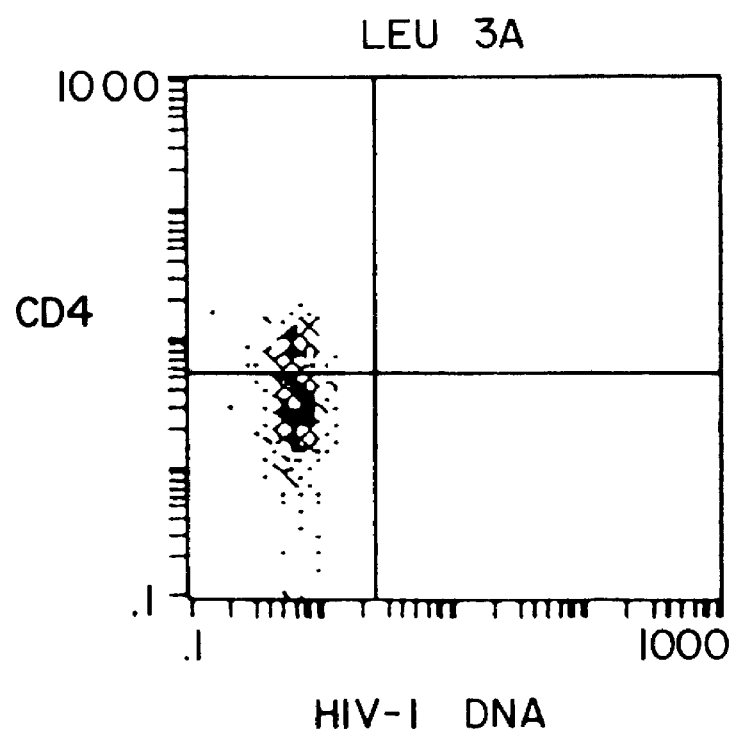
Figure 6D:
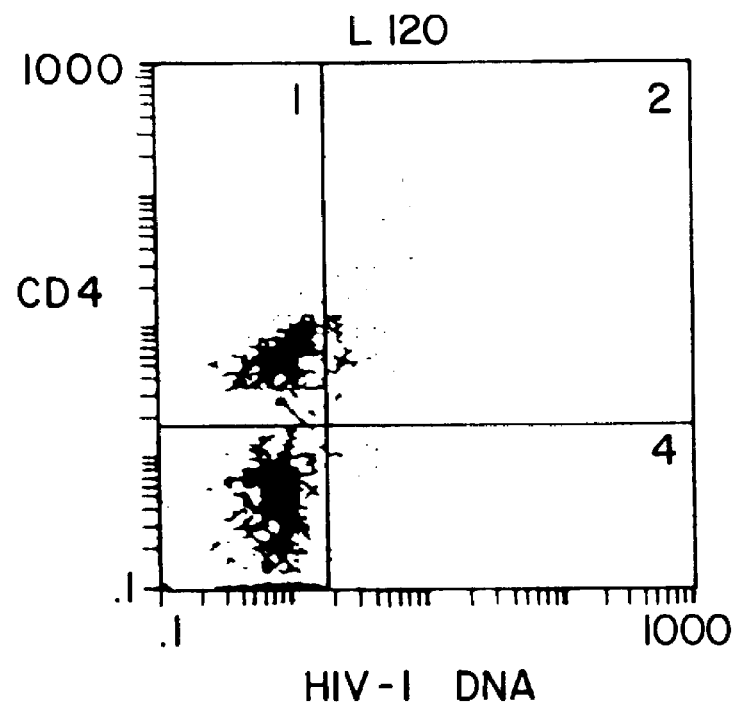
Figure 6E:
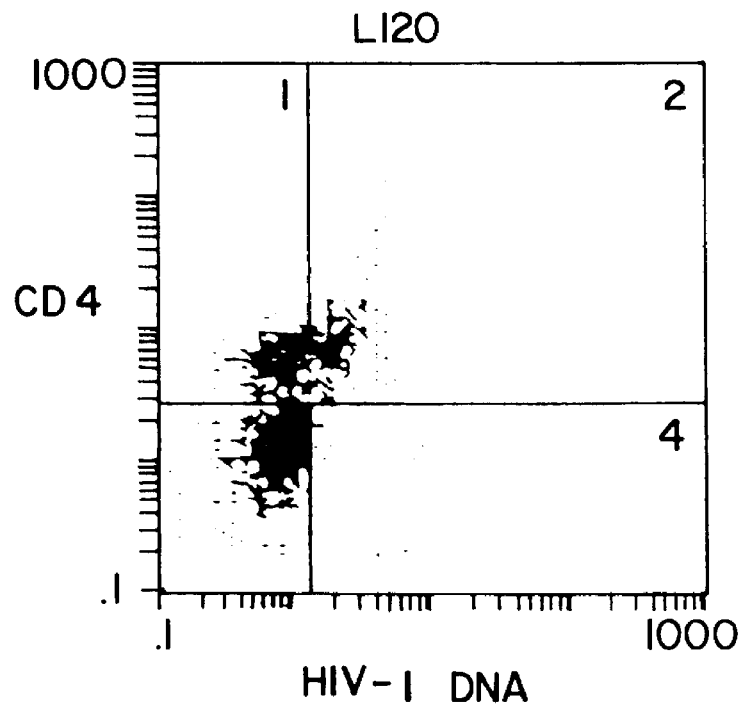
Figure 6F:
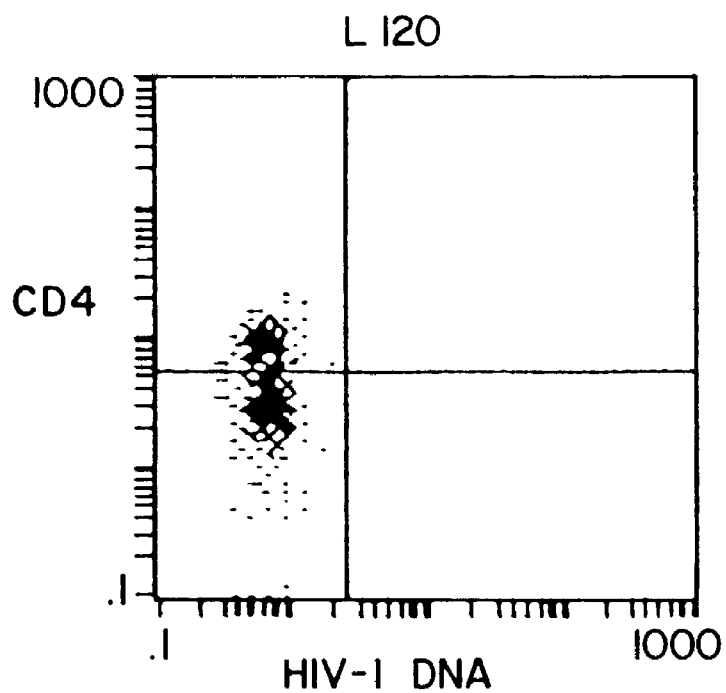
Figure 7A:
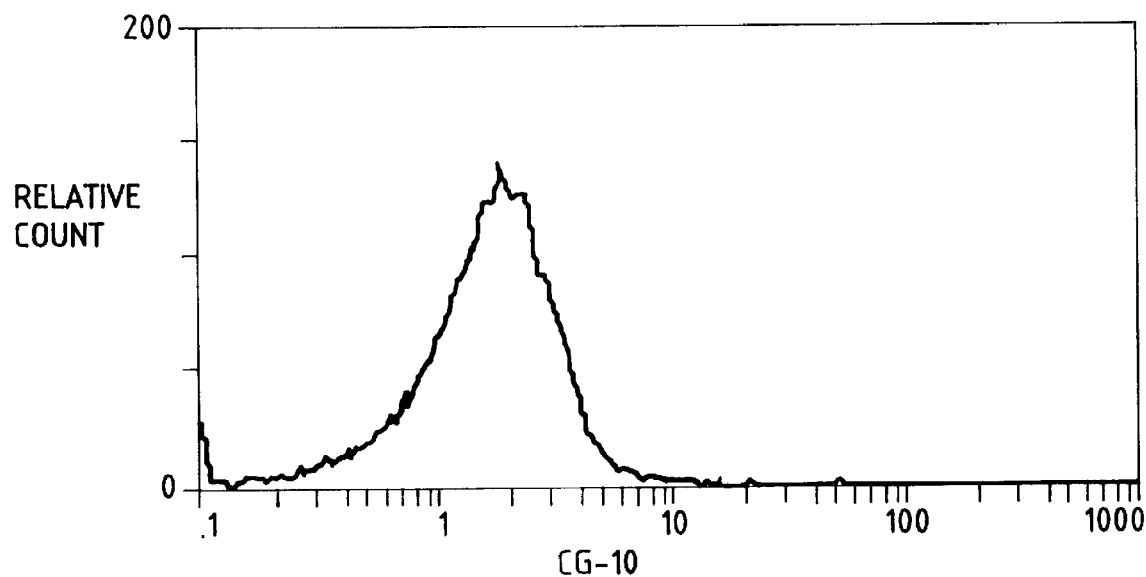
FIG. 7 shows single parameter histograms of PBMCs stained with CG-10, an antibody which binds CD4/gp 120 complexes. Histograms (A), HIV-1 infected CEM cells, (B) patient #5, and (C) patient #6 show populations of cells which stain for CD4/gp 120 on the cell surface. A HIV-1 seronegative patient sample (#14) lacks a CG-10-positive cell population.
Figure 7B:
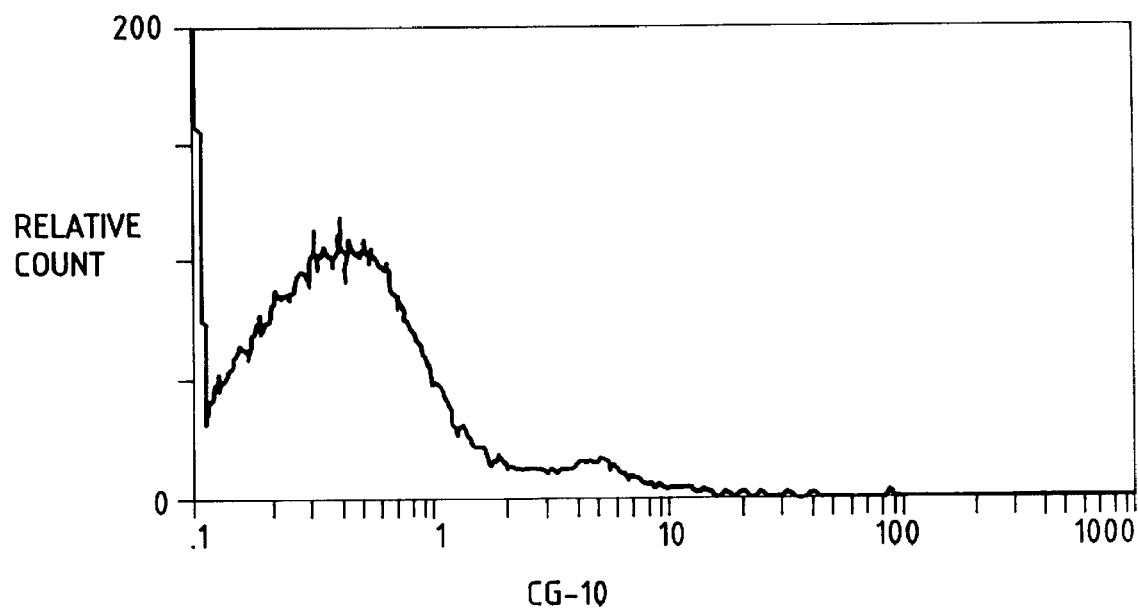
Figure 7C:
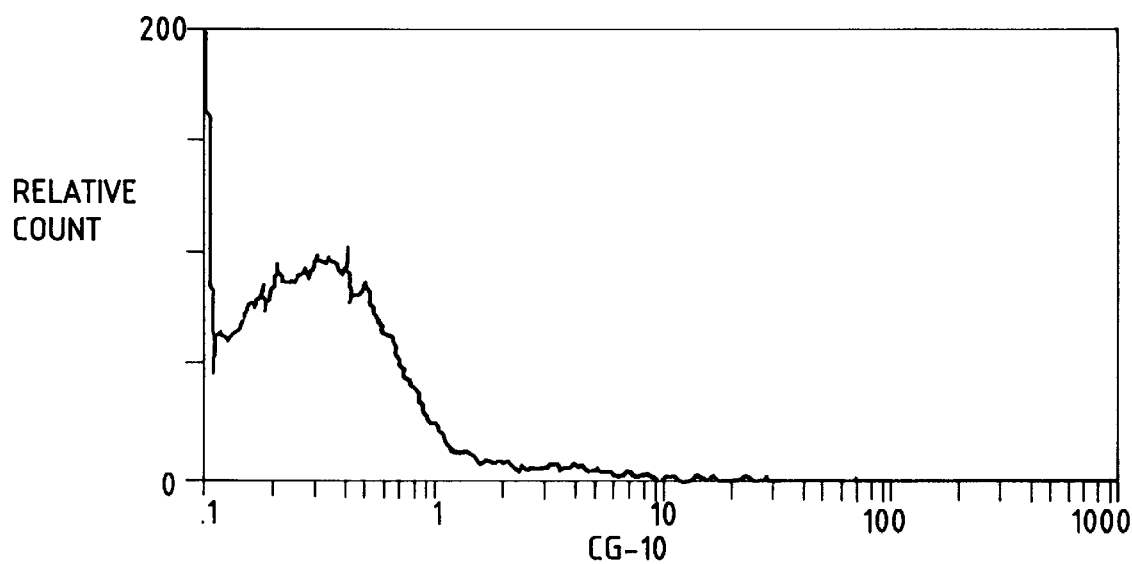
Figure 7D:
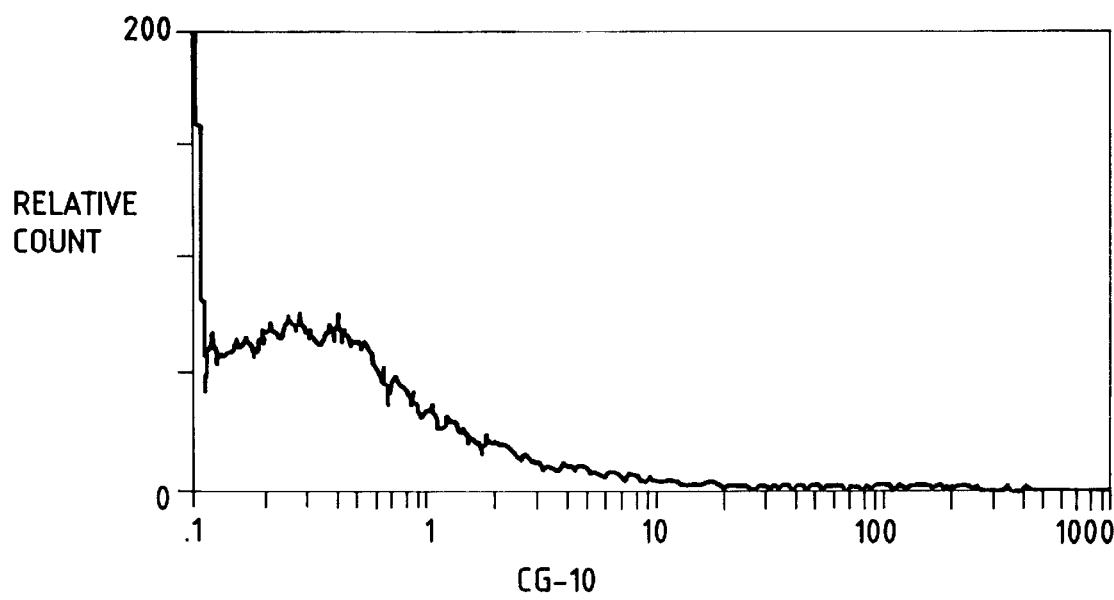

All samples were filtered through a 7 $\mu$m nylon mesh just prior to analysis. Samples were analyzed on the Coulter Electronica PROFILE II flow cytometer with POWERPAK option (Coulter Electronica, Inc., Hialeah, Fla.) at Veterans Lakesize Medical Center. Laser excitation was 15 mW at 488 nm and the standard optical filter configuration was utilized for fluorescence light detection (488 nm dichroic, 457–502 nm long pass laser blocking, 550 nm dichroic, 525 band-pass FITC fluorescence), 600 nm dichroic, and 635 nm band-pass (propidium iodide fluorescence filter). Instrument sensitivity was standardized before each experiment employing Immuno-Bright calibration beads (Coulter Source, Marriette, Ga.). Color compensation circuitry was adjusted using FITC only, PI only, and dual stained 100% HIV-1-positive cell samples. Standard curve showing the linearity of this assay is shown in FIG. 2. Sensitivity and specificity of this technique using the solution hybridization was 99.6% and 99.2% respectively (FIG. 3).

Three-Color Analysis of Cell Surface Markers

Monoclonal antibodies OKT4-FITC (Ortho diagnostics), CD3-PerCP (Coulter Diagnostics), and CD2-PE (Coulter Diagnostics) were employed for cell surface phenotyping. Peripheral blood mononuclear cells were re-suspended in 100 μl phosphate buffered saline (pH 7.4) and all antibodies were added at concentration recommended by the manufacturer. After thirty minutes incubation at room temperature the cells were fixed in 1% paraformaldehyde and analyzed by flow cytometry. The results of this analysis is shown in Table 2.

TABLE 2

IN SITU PCR for HIV-1 Proviral DNA
Correlation with CD4 Counts

| Patient Number | CD4 (% of PBMC) | HIV-1 DNA + (% of PBMC) |
|---|---|---|
| 1 | 14.3 | 15.0 |
| 2 | 28.3 | 3.2 |
| 3 | 35.2 | 1.4 |
| 4 | 0.1 | 4.2 |
| 5 | 0.2 | 0.0 |

The data presented in this table shows the detection of HIV-1 proviral sequences in HIV-1 infected patients. Patient No. 1 has symptoms of the disease and shows about 14% of the mononuclear cells being CD4+T-cells. Similarly, 15% of the mononuclear cells contain a HIV-1 proviral sequence. Patient No. 2 and 3 are asymptomatic and have higher T-cells percentages and lower HIV-1 proviral DNA percentages. Patients 4 and 5 are near death and show low T-cells and HIV-1 proviral DNA percentage. All patients are HIV-1 antibody positive.

EXAMPLE 2

In Situ RNA PCR

Lymphocytes were aliquoted and treated with fixative and proteinase K as described for DNA PCR, although all solutions were prepared with 0.1% Diethyl pyrocarbonate (DEPC) treated analytical reagent water (Mallinckrodt). Glassware and plasticware were used also treated with 0.1% DEPC prior to autoclaving.

To each 400,000 cell sample, 40 μl of reaction mixture for reverse transcription was added (10.0 units thermostable rTth DNA Polymerase (Perkin Elmer Cetus) 90 mM KCl, 100 mM Tris-HCl pH 8.3, 1.0 mM MnCl2, 200 μM each dGTP, dATP, dCTP, 125 μM dTTP, 4 μM dUTP-11-digoxigenin (Beorhinger Manheim), RNase Inhibitor 40 units (Perkin Elmer Cetus), 100 pmoles downstream primer. Samples were incubated for 15 minutes at 70° C. and placed on ice.

160 μl of PCR reaction mixture was then added (100 mMKCl, 10 mm Tris-Hcl pH 8.3, 0.75 mM EGTA, 0.05% Tween 20, 5.0% (v/v) glycerol (Chelating buffer-Perkin Elmer Cetus) 2 mM MgCl2, 100 pmoles upstream primer. Samples were taken from ice and placed in an automated thermal cycler with block temperature at 80° C. Cycling was then performed as previously described.

The primers used for RNA amplification (MF111, MF126) were provided by Dr. M. Furtado. 5869–5886 MF111 GCGAATTCATGGAKCCAGTAGATCCTA-GACTA (SEQ ID NO: 1) 8760–8733 MF126 GCTCTAGACTATCTGTCCCCTCAGCTACTGCTATGG (SEQ ID NO:2) flank a major splice site within the mRNA species which encodes the TAT protein.

Solution hybridization was then performed as described for DNA with a fluorescently labeled oligonucleotide probe which crosses the mRNA splice site (MFA-1) MFA-1 TTCTCTATCAAAGCAACCCACCTCCCAATC(SEQ ID NO:3).

Cells used as positive controls were CEM cells infected with NL4–3 HIV-1.

EXAMPLE 3

Simultaneous In Situ Amplification and Immunophenotyping

The persistent viral replication that follows viral infection during the period of clinical quiescence is associated with aberrations in T-cell function and either a stable, slowly declining, or precipitously declining CD4 T-cells may be a consequence of a number of potential immunopathogenic mechanisms. In addition to direct HIV-1-induced cytopathicity, several indirect mechanisms including syncytium formation, free gp120/gp 160-mediated cell killing, autoimmune reactions, and apoptosis mediated by CD4 cross-linking have been invoked to explain CD4 T-cell depletion in association with low-level virus replication. Recent estimated of high level plasma-free RNA and cell-associated DNA in blood and lymphoid tissue support a direct role for viral replication in disease pathogenesis.

Qualitative abnormalities of T-cell functions are characterized by a selective inability to proliferate to self-MHC class II-restricted antigens in vitro. This may occur by one of several potential immunopathogenic mechanisms. High-affinity binding of gp 120 to CD4 may impede the usual interaction of CD4 with class Ii MHC molecules on the surface of antigen-presenting cells. Alternatively, gp 120-CD4 binding may interfere with the T-cells-specific cytoplasmic tyrosine protein kinase p56$^{lck}$-mediatedignal transduction that follows ligand binding to the CD4 molecule or lead to specific cytokine secretion.

HIV-1 infection may also decrease the cell surface expression of CD4 and other molecules involved in the T-cell response. CD4 cell surface expression may be reduced by modulating CD4 transcription or by sequestration of CD4-HIV-1 glycoprotein precursor (gp 160)-p56$^{lck}$ complex in the endoplasmic reticulum. Alteration of the cell surface CD4 molecule has a net effect of causing T-cell function in vivo has been hampered by the technical inability to simultaneously study the CD4 surface molecule and the viral genetic material at a single-cell level.

To quantify the numbers of CD4$^+$ T-cells within a heterogenous cell population that harbor the virus, we performed simultaneous intracellular HIV-1 amplification and cell surface immunophenotyping. Thirteen HIV-1 infected study participants and seven uninfected controls were evaluated for intracellular DNA and CD4 surface staining by PCR-driven in situ hybridization and flow cytometry. To screen for potential changes in the CD4 surface molecule on infected cells, a subset of HIV-1 infected patients was also examined for altered binding of anti-CD4 to potential gp 120-occluded and unoccluded determinants of CD4. Our results show a significant proportion (17.3% to 55.5%) of CD4 T-cells in blood contain HIV-1 DNA. Additionally, we found a marked disparity in CD4 cell surface staining between HIV-1 infected and uninfected cell populations consistent with cell surface CD4 epitope masking. The latter observation could have implications for monitoring disease progression.

Thirteen patients with documented HIV-1 infection and seven uninfected patients were selected for study. None of the thirteen HIV-1-infected subjects had received any antiretroviral therapy for at least 90 days preceding venous blood sampling. Each patient had a relatively stable CD4 T-cell number for at least 18 months preceding blood sampling. All analyses were performed in a blinded fashion with respect to the HIV-1 infection status of the study subjects. Informed consent was obtained from all patients before enrollment into this study.

PBMCs were isolated from fresh heparinized blood layered on a Histopaque 1077 (Signa, St. Louis, Mo.) discontinuous density gradient and centrifuged at 600×g for 30 minutes at ambient temperature. The turbid layer was removed, washed twice with 3 volumes of RPMI and once with phosphate buffered saline (PBS). Monocytes were removed using unconjugated CD14 (Becton-Dickinson, San Jose, Calif.) and antihuman Ig coated magnetic beads (Dynal, Great Neck, N.Y.) using the manufacturer's protocol. The 8E5/LAV cell line (AIDS Research and Reagent Program, NIAD, NIH, Bethesda, Md.), containing a single copy of integrated HIV-1 proviral DNA per cell, was harvested at an early passage number and used as the HIV-1-infected cell copy number control.

Cell samples were adjusted to a final concentration of 1×10 cells/ml. A 40 Bl aliquot of each sample was centrifuged at 600×g for 2 min at ambient temperature. The supernatant was removed and the cell pellet re-suspended in 90 Bl of PBS and 10 Bl of biotinylated anti-CD4 (Becton-Dickinson, San Jose, Calif.). Cells were again centrifuged at 300 to 600×g for 2 minutes and the cell pellet was washed twice in PBS. The cells were then fixed and permeabilized by the addition of Permafix (Ortho Diagnostics, Inc., Raritan, N.J.) at ambient temperature for 60 minutes. Cells were then pelleted as above, washed with PBS and re-suspended in 190 Bl of PCR reaction mixture consisting of 10 mM Tris HCL (pH 8.3); 50 mM KCL; 1.5 mM $MgCl_2$; 0.25 mM each dATP, dCTP, dGTP; 0.14 mM dTTP; 4.3 BM dUTP-11-digoxigenin; 100 pmole each forward and reverse primer; 1.0 Bl (5 units) Taq polymerase (Amplitaq, Perking-Elmer Cetus, Norwalk, Conn.) and gelatin 0.001% w/v.

The DNA in the reaction mixture was amplified in 500 Bl tubes inserted into the wells of a 48 well thermocycler (Perkin-Elmer Cetus, Norwalk, Conn.) programmed for 25 cycles (94° C.; 1 minute), primer annealing (58AC; 2 minutes), and primer extension (74° C.; 1.5 minutes), with 5 seconds added for each of 25 cycles. Appropriate positive and negative controls amplified with or without the addition of Taq polymerase were simultaneously run with each sample.

After in vitro amplification, cells were pelleted and re-suspended in 25 Bl of 10 mM Tris HCL (pH 8.3), 50 mM KCL, and 1.5 mM $MgCl_2$. A 100 ng aliquot of the appropriately labeled target specific oligonucleotide probe in 10 Bg/ml sonicated herring sperm DNA (Sigma, St. Louis, Mo.) was added to the reaction tube. The product DNA was denatured at 95° C. for 3 minutes, then allowed to hybridize with the respective oligonucleotide probe at 56° C. for 2 hours. After hybridization, the cells were washed for 30 minutes with 2×SSC/50% formamide/500 g/ml BSA at 42° C., 30 minutes with 1×SSC/5 BG/ml BSA at ambient temperature and then briefly with PBS at ambient temperature.

After the last wash, the cells were re-suspended in 90 Bl of PBS and 20 Bl streptavidin-phycoerythrin (PE) and incubated for 30 minutes at ambient temperature. The cells were then washed in PBS as described above. The cell suspension was filtered through a 37 Bm nylon mesh and analyzed by flow cytometry using an EPICS PROGILE III flow cytometer. Laser excitation was 15 mW at 488 nm, and the FITC and PE fluorescence was detected with standard optical filter set-up (550 dichroic, 525 bandpass (FITC) and 585 bandpass (PE)). Instrument sensitivity was standardized before each experiment employing Immuno-Bright calibration beads (Coulter Source, Marriette, Ga.). The percent fluorescence-positive cells was determined by integration over a range of 0.2% positive counts on the identically treated negative sample (100% uninfected PBMCs).

Sequence-specific oligonucleotide probes (Applied Biosystems, San Diego, Calif.) containing 5'- and 3'-labeled 5-carboxyfluorescein were synthesized on an Applied Biosystems 380B DNA synthesizer using 5' carboxyfluorescein phosphoramidite. The synthesized material was alkaline deprotected and purified by high-performance liquid chromatography. 5'-carboxyfluorescein phosphormamidite incorporation was verified by ultraviolet spectroscopy. HIV-1 gag primers SK39 and G51 (Becton-Dickinson) and HLA-DQ% primers GH26/27 were used as target sequence specific and control primers, respectively.

Immunophenotyping was performed using antibody concentrations and protocols recommended by the manufacturers. Antibodies used included: biotinylated anti-CD5 (Leu 1); anti-CD4 (Leu3A); Bl 120; and unconjugated anti-CD14 (Leu M3) (Becton-Dickinson, San Jose, Calif.). FITC-conjugated anti-CD4 (Caltag, San Francisco, Calif.), and PE-conjugated anti-CD4 (Coulter, Hialeah, Fla.) were used in experiments to determine antibody stability during thermal cycling. Comparisons of the relative intensity of cell surface staining was done by determining the mean peak fluorescence of the selected groups. CG10, an antibody which binds to CD4/gp 120 complexes. was used for cell-surface marker staining and was generously provided by Jonathan Gershoni of Tel Aviv University.

Statistical analysis of pre-and post-cycling determinations of cell surface markers was performed using chi-square analysis. Comparison of mean peak fluorescence differences was performed using paired t-tests.

To determine the percentage of specific subpopulations of cells and to monitor possible selective loss of certain subpopulations of cells during thermal cycling, fluorescein-conjugated monoclonal antibodies specific for T-cell antigens were used for immunophenotyping. Magnetic bead enrichment of lymphocytes was performed following Ficoll-Hypaque discontinuous density gradient separation of PBMCs to ensure the absence of monocytes in populations of cells with decreased CD4 (Leu3A) expression. Negative sorting using anti-CD14 resulted in at least 90% lymphocytes with less than 2% monocytes in all samples. The pre-cycling percentage of cells expressing the CD4 (L 120 and Leu 3A) and CD5 cell surface antigens following enrichment did not differ from the post-cycling percentage of cells expressing these antigens ($p > 0.2$ for all Ktests).

A variety of antibody conjugations was used in immunophenotyping experiments to determine resiliency during thermal cycling. Biotinylated anti-CD4 was bound to cells before fixation without subsequent thermal cycling (See FIG. 4, panel B), before fixation with subsequent thermal cycling (See FIG. 4, panel C), and after fixation and thermal cycling (See FIG. 4, panel D), biotin-conjugated anti-CD4 produced results comparable to uncycled controls (See FIG. 4, panel A).

Direct PE conjugate antibodies lost fluorescence following thermal cycling and direct FITC conjugated anti-CD4 bound non-specifically to >90% of cells when bound before or after thermal cycling. Biotin and PE conjugated anti-CD4 added after thermal cycling failed to detect CD4 expressing cells. Based on these results, dual immunophenotyping and in situ hybridization was performed using biotin-conjugated anti-CD4 that was bound to the cell surface before fixation and thermal cycling. This antibody labeling scheme ensures that cell surface marker determinations on cycled cells can be extrapolated to uncycled cells.

Quantification of CD4 T-cells harboring proviral DNA was determined by PCR-driven in situ hybridization and two-color flow cytometry, using simultaneous immunophenotyping with the anti-CD4 antibody Leu 3A and with HIV-1 gag-specific primer pairs and a fluorescein-labeled target-specific probe. The percentage of CD4 cells was determined following monocyte depletion in order to restrict our analysis to CD4 T-cells. The percentage of CD4 T-cells harboring HIV-1 proviral DNA ranged from 17.3% to 55.5% with a median of 40.5%, while the percentage of infected PBMCs ranged from 3.6% to 15.6% with a median of 10.1%. Negative controls consisting of: PBMCs isolated from an HIV-1 uninfected donor amplified and probed with HIV-1-specific aligonucleotides; HIV-1-infected 8E5 cells and PBMCs isolated from an HIV-1-infected donor amplified with HIV-1-specific primers and probed with an internally conserved oligonucleotide probe without Taq polymerase; and HIV-1 positive cells and PBMCs amplified with HLA DQ% primers and probed with a HIV-1-specific oligonucleotide probe all lacked HIV-1-positive cell subpopulations. The percentage of infected PBMCs or CD4 T-cells did not correlate with CD4 T-cell number or CD4 percentage in these patients. The results of these studies are summarized below in Table 3.

determine if there was any selective loss of T-cell subsets, an antibody directed against the pan-T-cell marker CD5 was used.

The total numbers of CD4 T-cells in a given blood sample were comparable, regardless of being enumerated before thermal cycling or after thermal cycling with or without DNA amplification and resolution into specific subpopulations. These results indicated that there was no selective loss of this T-cell subpopulation. Additionally, among these two T-cell subpopulations in each of the 13 tested HIV-1 positive clinical samples, the mean peak fluorescence of Leu3A stained cells was consistently decreased by 1.5 to 3-fold in the CD4 positive, HIV-1 proviral DNA positive population when compared to the CD4 positive, HIV-1 proviral DNA negative cell population (Table 3, FIG. 5). In 12 of the 13 patient samples, the CD4 positive, HIV-1 proviral DNA positive T-cells appeared as a single population with a decreased mean peak fluorescence. In one sample (FIG. 5, patient #6), the CD4 positive, HIV-1 proviral DNA positive T-cells formed two subpopulations; one subpopulation with slightly decreased Leu3A cell surface staining, and the other with a phenotype approaching CD4 negative. In this group of patients, the decreased Leu3A cell surface staining is statistically significant by $\chi^2$ analysis (p<0.001). The resolution into the two subpopulations following PCR-driven in situ hybridization and flow cytometry with Leu3A approximated the dot-plot distribution observed by flow cytometry with Leu3A without target DNA amplification. To screen for the range of values for mean peak fluorescence intensity, the 7 HIV-1 uninfected subjects were evaluated. Each determination was performed in duplicate. Among these 7 subjects, the mean peak fluorescence intensity values ranged from 2.3 to 11.2.

TABLE 3

PCR-Driven In Situ Hybridization Results

| | | | HIV-1 DNA Positive Cells | | Mean Peak Fluorescence (Leu3A-PE) | |
|---|---|---|---|---|---|---|
| Patient | CD4 Count | CD4 % | % of PBMCs** | % of CD4 + Cells | CD4 + HIV −≠≠ | CD4 + HIV + |
| 1 | 11 | 19.2 ± 2.3 | 8.1 ± 2.1 | 42.01 | 2.7 ± 0.2 | 1.8 ± 0.2 |
| 2 | 20 | 23.6 ± 1.4 | 4.1 ± 0.6 | 17.3 | 2.9 ± 0.2 | 2.1 ± 0.2 |
| 3 | 85 | 9.2 ± 0.6 | 4.2 ± 0.9 | 45.6 | 6.8 ± 0.4 | 3.8 ± 0.2 |
| 4 | 98 | 22.3 ± 1.6 | 5.0 ± 1.2 | 22.4 | 8.5 ± 0.1 | 3.8 ± 0.2 |
| 5 | 259 | 27.7 ± 0.4 | 14.2 ± 1.6 | 51.2 | 2.8 ± 0.1 | 2.0 ± 0.1 |
| 6 | 263 | 19.0 ± 0.7 | 8.4 ± 1.4 | 44.2 | 9.2 ± 0.1 | 3.7 ± 0.2 |
| 7 | 372 | 28.1 ± 1.2 | 15.6 ± 0.5 | 55.5 | 9.1 ± 0.6 | 6.2 ± 0.1 |
| 8 | 420 | 26.5 ± 1.5 | 11.5 ± 1.1 | 43.3 | 5.5 ± 0.3 | 2.2 ± 0.2 |
| 9 | 506 | 27.1 ± 1.2 | 11.0 ± 1.3 | 40.5 | 6.1 ± 0.2 | 4.7 ± 0.7 |
| 10 | 513 | 19.0 ± 1.1 | 3.6 ± 0.5 | 18.9 | 8.8 ± 0.4 | 6.1 ± 0.2 |
| 11 | 530 | 31.1 ± 1.3 | 10.4 ± 0.7 | 33.2 | 9.8 ± 0.5 | 5.6 ± 0.3 |
| 12 | 742 | 30.4 ± 0.4 | 10.1 ± 2.7 | 33.2 | 9.6 ± 0.5 | 4.6 ± 0.5 |
| 13 | 1431 | 39.3 ± 0.7 | 14.9 ± 0.8 | 37.9 | 12.4 ± 0.2 | 4.5 ± 0.5 |
| 14 | 1046 | 35.7 ± 1.2 | 0 | 0 | 11.2 ± 0.4 | 0 |

**Monocyte depleted
≠≠Mean peak fluorescence of Leu 3A staining on CD4+ cells from 7 additional uninfected controls ranges from 2.3–11.2

To determine the association of HIV-1 infection with CD4 conformation and cell surface expression on cells containing HIV-1 proviral DNA, PCR-driven in situ hybridization and two-color flow cytometry was used with a panel of antibodies directed at multiple epitopes. A conformation epitope of CD4 associated with the gp 120-CD4 binding site was screened by Leu3A, the prototype anti-CD4 antibody in commercial use. An epitope in CD4 domain 4, distal from the HIV-1 gp 120 binding site, was screened using L120. To determine if the altered CD4 cell surface staining properties for cells harboring HIV-1 proviral DNA are a result of CD4 antigen downregulation or modification, split lymphocyte samples from 4 patients 4, 5, 12, and 13 and seronegative control patient #14 were stained with either anti-CD5, Leu3A or L120, and analyzed for the presence or absence of HIV-1 product DNA. There was concordance among the CD4 T-cell numbers as determined by the total numbers using anti-CD5 relative to the sum of the CD4 T-cell numbers as determined by the total numbers using anti-Cd5 relative to the sum of the CD4 T-cell subpopulations using Leu3A or L120. In contrast to the decreased mean peak fluorescence observed for the CD4 positive, HIV-1 proviral DNA positive T-cells using Leu3A, there was no statistical difference (p=0.14) in the mean peak fluorescence observed for this population using L120 (Table 3, FIG. 6).

HIV-1 infection of T-cells and cells of the monocyte-macrophage lineage required gp 120-mediated binding of the virion to the host cell CD4 surface molecule. The CD4-gp 120 interaction involved high affinity binding of discontinuous sites of gp 120 with the first immunoglobulin-like domain of CD4. Changes in the molecular conformation of CD4 are presumed to allow direct fusion of the virus and host cell membranes that is mediated by the amino terminal fusion domain of the envelope transmembrane glycoprotein (gp41). The nucleocapsid core then enters into the host cell cytoplasm, where the virion is uncoated and the viral RNA molecule is reverse transcribed into DNA. After translocation to the cell nucleus, the viral genome can persist in a latent chronically infected or productive state. A large proportion of these viral genomes are excluded from the replicating virus pool by virtue of being either genotypically or phenotypically defective.

The molecular events responsible for CD4 T-cell depletion and qualitative abnormalities of T-cell function have not been clearly delineated. Both indirect and direct immunopathogenic mechanisms postulated to explain these findings have been predicated upon the estimated numbers of HIV-1-infected cells. While a large proportion of infected cells would be compatible with direct HIV-i-induced cytopathicity, small numbers of HIV-i-infected cells require an indirect mechanism to account for the specific loss of the CD4 T-cell population. Therefore, determining the magnitude of the reservoir of virus in vivo and characterizing the virus-host cell interaction has significant implications for our understanding of viral pathogenesis.

The present invention discloses that a significant proportion (up to 50%) of CD4 T-cells can harbor virus in an HIV-1 infected individual. These results are comparable with earlier studies that also found a large proportion of blood and tissue cells to harbor proviral DNA. One significant technical limitation to earlier reports was, however, that heterogenous cell populations were not fractionated to elucidate the numbers of infected cells which express the CD4 surface antigen. Quantification of proviral DNA in purified CD4 T-cell populations provided a wide range of estimates (1 in 10,000 to 1 in 10) of the proportion of blood cells that were infected with HIV-1. Cell homogenization and proviral DNA quantification predicated upon analysis of product DNA in solution have significant technical limitations compared to specific intracellular localization of viral sequences.

HIV-1 proviral DNA is present in 3.6% to 15.6% of PBMCs. For the monocyte-depleted CD4 T-cells, however, HIV-1 proviral DNA is present in 17.3% to 55% of cells. The difference in the proportion of infected CD4 T-cells was not related to the subject's CD4 T-cell counts. The apparent disparity between the stage of disease and the proportion of HIV-1 infected cells can be attributed to the fact that enumerating the numbers of infected cells is a static measure of a dynamic process.

Simultaneous immunophenotyping with intracellular nucleic acid amplification also revealed a disparity in the cell surface staining characteristics observed for HIV-1 infected and uninfected cells in a single sample and difference CD4 epitopes in a split sample. To determine if HIV-1 affects CD4 cell surface expression or conformation in vivo, CD4 epitope mapping was performed using anti-Leu3A, an antibody which binds to an epitope overlapping the HIV-1 binding site in domain 1, anti-L120, and antibody which binds to a CD4 epitope in domain 4 that is unaffected by HIV-1 binding, and anti-CD5, a pan-t-cell marker also unaffected by HIV-1 infection. In the same patient sample preparation, simultaneous determinations of cell surface staining for CD4 by Leu3A or L120 and intracellular HIV-1 product DNA revealed a 1.5 to 3 fold decrease in Leu3A (CD4) staining in infected cells compared to uninfected cells. There was, however, no difference in the staining intensity of the L120 antibody for the two cell populations.

While HIV-1 associated changes in CD4 cell surface expression may be a consequence of blocked antibody access to or conformational changes in the CD4 molecule, decreased CD4 transcription or translation, or intracellular CD4 sequestration, the present results support the hypothesis the HIV-1 induces cell surface CD4 epitope masking. The epitope masking may be the result of gp 120/gp160-CD4 interactions. This would account for the greater signals obtained using L120 in place of Leu3A; the former epitope is not occluded by gp 120, while the latter epitope is occluded. Only two of these 13 HIV positive patients (patients 5 and 6) had cells which expressed gp 120/CD4 complexes as measured by CG-10 cell surface staining. Of these two patients, C-10 cell surface staining was observed in approximately 9.1% of PBMCs from patient 5, and 4.0% of PBMCs from patient 6 (See FIG. 7). Alteration of the cell surface staining characteristics likely results from gp 160 binding to CD4 before CD4 is expressed on the cell surface. The intracellular gp 160-CD4 complex can, however, be recirculated to the endoplasmic reticulum, without presenting to the cell surface. Previous studies have shown that intracellular CD4-gp 160-p56$^{lck}$ complexes are OKT4 positive and OKT4A, an antibody that binds to an epitope similar to Leu3A, negative. This phenotype is similar to the CD4 cell surface staining characteristics we observed for all of the HIV-1 DNA positive study patients.

The significant proportion of CD4 T-cells infected with HIV-1 and the associated alteration of the CD4 cell surface molecule in these infected cells suggests that myristylated tyrosine protein kinase p56$^{lck}$ is required for co-receptor mediated signal transduction. In the absence of co-receptor engagement, stimulation of the TCR results in a diminished response. T-cell activation may, therefore, be inhibited as a consequence of the gp 120-CD4 interaction. Perturbations of CD4 prior to TCR-mediated signal transduction may also induce apoptosis. HIV-1-mediated T-cell destruction by apoptosis can be induced in uninfected cells by exposure to soluble gp 120, then activation through the TCR. Additionally, apoptosis can be induced in T-lymphoblast acutely infected with HIV-1. Although a soluble gp 120-CD4 interaction is sufficient to induce apoptosis in uninfected cells in vitro, the large reservoir of persistently infected CD4 T-cells with altered CD4 cell surface expression in vivo can account for programmed cell death following TCR activation.

Although the invention has been described primarily in connection with special and preferred embodiments, it will be understood that it is capable of modification without departing from the scope of the invention. The following claims are intended to cover all variations, uses, or adaptations of the inventions following, in general, the principles thereof and including such departures from the present disclosure as come within known or customary practice in the field to which the invention pertains, or as are obvious to persons skilled in the field.

What is claimed is:

1. An in situ process of simultaneously detecting a specific predetermined nucleic acid sequence and a specific predetermined cellular antigen in the same intact cell, the process comprising the steps of:
(a) labeling the antigen with a biotin- or DNP-tagged antibody that specifically binds to the antigen;
(b) exposing the antigen-labeled cell to a water-soluble fixative and permeabilization agent;
(c) amplifying the specific nucleic acid sequences in the cell in the presence of deoxyribonucleotide triphosphates coupled to a molecule that prevents diffusion of amplified sequences from the cell;
(d) labeling the amplified nucleic acid sequences with a fluorescently-tagged nucleic acid probe that specifically hybridizes to the amplified nucleic acid sequences; and
(e) detecting the labeled nucleic acid sequences and labeled cellular antigen, by determining the presence of the fluorescently-tagged probe and the biotin or DNP-tagged antibody, respectively.

2. An in situ process of simultaneously detecting HIV-1 proviral DNA and cell surface CD4 antigen in intact T cells, the process comprising the steps of:
(a) labeling the CD4 cell surface antigen of the T cells with a biotin- or DNP-tagged antibody that specifically binds to the CD4 cell surface antigen;
(b) exposing the antigen-labeled cells to a water-soluble fixative and permeabilization agent;
(c) amplifying the HIV-1 proviral DNA nucleic acid sequences in the cells in the presence of deoxyribonucleotide triphosphates coupled to a molecule that prevents diffusion of amplified sequences from the cell;

(d) labeling the amplified HIV-1 proviral DNA sequences with a fluorescently-tagged nucleic acid probe that is complementary to the HIV-1 proviral DNA sequences; and (e) detecting the labeled HIV-1 proviral DNA nucleic acid sequence and labeled CD4 cell surface antigen by fluorescence activated flow cytometry, by determining the presence of the fluorescently-tagged probe and the biotin or DNP-tagged antibody, respectively.

3. The process of claim 1, wherein the molecule is digoxigenin.

4. The process of claim 2, wherein the molecule is digoxigenin.

5. The process of claim 1 wherein the specific nucleic acid sequence is a DNA sequence.

6. The process of claim 1 wherein the specific nucleic acid sequence is a RNA sequence.

7. The process of claim 1 wherein the specific nucleic acid sequence is a viral nucleic acid sequence.

8. The process of claim 7 wherein the viral nucleic acid sequence is an HIV sequence.

9. The process of claim 8 wherein the HIV sequence is HIV-1 proviral DNA.

10. The process of claim 1 wherein the cellular antigen is a cell surface antigen.

11. The process of claim 10 wherein the cell surface antigen is involved in T cell activation.

12. The process of claim 11 wherein the cell surface antigen is CD4.

13. The process of claim 1 wherein the intact cell is a white blood cell.

14. The process of claim 13 wherein the white blood cell is a peripheral mononuclear cell.

15. The process of claim 14 wherein the peripheral mononuclear cell is a T cell.

16. The process of claim 1 wherein detecting is accomplished by fluorescence activated flow cytometry or fluorescence microscopy.

17. The process of claim 1 wherein the cell is a T cell, the specific nucleic sequence is HIV-1 proviral DNA and the cell surface antigen is CD4.

* * * * *